(12) United States Patent
Zhao

(10) Patent No.: US 7,407,626 B2
(45) Date of Patent: Aug. 5, 2008

(54) COMPOSITION AND METHOD OF USE OF MEDICAL TEST KIT

(76) Inventor: Qing-Hua Zhao, No. 5, Lane 248, Xinshi Road., Shanghai, 200083 (CN)

( * ) Notice: Subject to any disclaimer, the term of this patent is extended or adjusted under 35 U.S.C. 154(b) by 877 days.

(21) Appl. No.: 10/829,059

(22) Filed: Apr. 20, 2004

(65) Prior Publication Data
US 2005/0232814 A1    Oct. 20, 2005

(51) Int. Cl.
    *G01N 33/48* (2006.01)
(52) U.S. Cl. ............... 422/61; 436/8; 436/63; 436/86; 436/95; 436/97; 436/79; 436/110; 436/128; 436/163; 436/166; 436/183; 435/14; 435/22
(58) Field of Classification Search ............ 422/55, 422/61, 99; 436/8, 12, 14, 15, 63, 66, 95, 436/97, 86, 79, 106, 110, 128, 163, 166, 436/183; 435/14, 22
See application file for complete search history.

(56) References Cited

U.S. PATENT DOCUMENTS

| | | | | |
|---|---|---|---|---|
| 4,184,850 A | * | 1/1980 | Habenstein | 436/128 |
| 4,275,031 A | * | 6/1981 | Fischer et al. | 422/57 |
| 5,137,692 A | * | 8/1992 | Fritz | 422/61 |
| 5,260,219 A | * | 11/1993 | Fritz | 436/71 |
| 5,801,059 A | * | 9/1998 | Smith et al. | 436/128 |
| 6,203,757 B1 | * | 3/2001 | Lu et al. | 422/58 |
| 6,319,665 B1 | * | 11/2001 | Zwanziger et al. | 435/5 |
| 6,833,111 B2 | * | 12/2004 | Robertson et al. | 422/58 |
| 2004/0138688 A1 | * | 7/2004 | Giraud | 606/181 |

* cited by examiner

*Primary Examiner*—Maureen M Wallenhorst
(74) *Attorney, Agent, or Firm*—Raymond Y. Chan; David and Raymond Patent Firm

(57) ABSTRACT

A medical test kit includes a glucose testing composition, a protein testing composition, a bilirubin testing composition, a bilinogen testing composition, an amylase testing composition, a blood testing composition, a calcium testing composition, a nitrite testing composition, a ketone testing composition and a pH testing composition. The medical test kit also includes a plurality of corresponding indicative spectra to each of its units such that a health condition of a user can easily be interpreted. Furthermore, an interactive reference chart is provided for guiding a user for the use of the kit. The kit is suitable for use for the public and is capable of encouraging self health care of society.

16 Claims, 15 Drawing Sheets

FIG. 3A

'+': Unhealthy condition: treatment required
'?': Doubtful condition: early alert for unhealthy condition
'0': Healthy condition "o" indicates a condition below the threshold showing good health
"?" indicates a condition of average threshold showing a doubt health
"+" indicates a condition above the threshold showing bad health

COMPOSITION AND METHOD OF USE OF MEDICAL TEST KIT

BACKGROUND OF THE PRESENT INVENTION

1. Field of Invention

The present invention relates to a medical test kit, and more particularly relates to a urine test kit comprising a plurality of chemical compositions for testing urine glucose, urine protein, urine bilirubin, urine bilinogen, pancreatic amylase, urine hemoglobin, urine calcium, urine nitrite, urine ketone, and urine pH, wherein the urine test kit employs simple procedures and provides a convenient and indicative measure, which is capable of showing a health condition of a user and serving as a preliminary screening test for a number of chronic disease.

2. Description of Related Arts

Diseases may not be a health hazard if we are capable of discovering or recognizing the existence of the diseases at an early stage. This is difficult because this means that we are able to listen to the signals from our bodies which may be insignificant to our feelings. A more reliable and scientific way is to having a body check in a clinic or in a hospital on a regular basis, but this is time consuming and expensive, and this may also employ complicated laboratory tests which require artificial sample extraction from our body, such as blood extraction, with the inherent risks such as tools and equipment contamination which may result in transmission of a disease. For a healthy person who is asymptomatic, it may not worth to take this risk of a body check.

Urine is an ideal indicator for many tests and is also a very good alternative to many blood tests. The chance of contamination is low and the large number of components in urine are good indicators to different diseases. However, problems of urine storage and urine testing methods make it undesirable to use urine as a sample for chemical analysis. Special storage arrangement for urine is required to prevent the oxidation of active components in urine or the photochemical reaction occurred under sunlight. On the other hands, in order to obtain a precise and representative result, a highly sensitive urine testing method must be used. Thus, the existing methods either require a very high precision measuring machine or a manual laboratory test conducted by a skillful technician. It is impossible for a person to carry out the urine test by himself for obtaining a preliminary screening test result when the health of the person is in doubt, or for a patient to carry out the urine test by himself for monitoring his disease. In case of those patients suffered from chronic illness, it is especially important that self-monitoring of their health is made possible, or a comprehensive health testing method is provided such that they can easily obtain their health conditions which is crucial for having good control of their chronic disease and preventing complications which is more serious induced by poor control of their chronic disease.

Traditional medical tests employing laboratory tests with chemical analysis are highly recognized as being effective, consistent, and reliable over the world. Medical tests are usually required to be carried out under a special environment, such as a laboratory in a hospital, a clinic, or a health center, and the tests are conducted by a specialist or a laboratory technician. However, since the traditional medical tests usually are conducted manually, require a long time period, acquire a series of complicated steps, require the use of testing solution having a short storage period, and employ heating or boiling steps which may induce a predetermined level of danger, the traditional medical tests employing laboratory tests, are gradually replaced by test machines. For example, many urine tests are now conducted by the use of automatic urine biochemical testing apparatus.

Though most medical tests for the presence of components in the urine are capable of being conducted in a laboratory, it is very important to provide self-administered medical tests which is cost effective and time saving, acting as a preliminary indicator for health of the general public. In this way, the early stage detection of disease which allows immediate treatment of the disease will highly reduce the chance of development of the more serious disease. This early awareness of the disease is an important warning signal which allows a patient to identify the initiate onset of a disease, such that the patient may actively alter his lifestyle to prevent any development of disease, to rectify any bad habits which is harmful to his health, and to self monitoring his health. On the other hand, the patient is able to consult a doctor and receive suitable treatment at an early stage of a disease, which in turn will highly increase the chance of curing the disease.

Self administered medical tests also allow a patient to have a better understanding of his health conditions, persuading him to face his disease and guiding him to realize any effects resulted from his acts in his daily life. The self administered medical tests results are good reminder to the patient of his health conditions which can positively guiding the patient to follow his treatment plan and hence highly increase the chance of recovery. Furthermore, the active monitoring of treatment with self administered medical tests can reduce the chance of inappropriate treatment because the self administered medical tests can reflect the present health conditions and the body's response to the treatment immediately.

It is especially true for outpatients having those illnesses required continuous management and self-control by themselves. In the disease development pathway, starting from healthy to early stage of disease and to chronic disease, further developing to serious disease, and finally to the end of life due to disease, self-administered tests play a very important role in control and management of disease, and hence preventing the development of more serious complications and diseases in the disease development pathway.

Furthermore, self administered medical tests can also reduce the dependence of patients, initiating a medical revolution towards a two ways management, and reduce the medical expenses. The patient is allowed to put an effort towards his treatment and lessen the burden of the medical practitioners, which in turn lessen the stress of the ever heavy workload of the medical practitioners and hence reserving the resources for the need. Moreover, the two ways management of disease is much more effective and efficient because the key to recovery depends heavily on the patient himself, while the self administered medical tests can provide him a better understanding of his health and serve as a guideline towards recovery.

Diabetes mellitus is a worldwide common disease that the early stage and the asymptomatic period are difficult to diagnosis in general clinical practices. Diabetes is a chronic disease, and without proper treatment, diabetes will lead to the development of serious complications in 15 to 20 years including cardiovascular and cerebrovascular disease, hypopsia, eye degeneration, and high blood viscosity symptom. Patients suffering from diabetes are usually not aware of the disease and unable to discover the disease unless serious complications have been developed after many years. Present diagnosis of the disease rely heavily on the renal blood glucose level with the threshold value of blood glucose level 160 mg %. However, common glucose tests, including single blood glucose tolerance test, single blood glucose test, and single intravenous blood glucose test, are inadequate for diagnosis of the early stage of diabetes, and require the patients to go to the hospitals or clinics for blood extraction and testing with sophisticated apparatuses or meters, while personal continuous daily examinations and monitor on a regular basis are not possible, convention diagnoses are inadequate and insufficient to provide a reliable and realistic method for acting as an initial screening of the disease, even for those in the high risk class.

Kidney disease is another common disease which is difficult to be detected during the early kidney impairment and the asymptomatic period except using medical test analysis. Many diseases such as high blood pressure, diabetes mellitus, rheumatic fever will impair cardiovascular systems especially the blood capillary including the glomerular capillary. The effect of high blood pressure, diabetes mellitus and rheumatic fever will gradually lead to the development of kidney failure, that the low molecular protein, such as the albumin, will undergo abnormal filtration process. If the situation is not recognized immediately, without any suitable treatment the seriousness of the disease will be increased which will give rise to the excretion of large molecules. Kidney failure is a serious disease which will endanger the life of the patient.

Liver disease is another common disease. Liver is a complicated and important organ which is crucial to many physiological process including detoxication and elimination of hemoglobin. Since liver is a large organ generally with a mass of 1.5 kg in an adult, with a high metabolic activity and a high cell regeneration ability, it is not easy to diagnosis any localized damage to the liver with the common convention liver function tests unless a substantial portion of the liver is affected and the situation is serious. Existing indicators for liver function are urine bilirubin and urine bilinogen which are the metabolites produced from liver.

Substantive liver damage will affect the absorption, binding, and excretion of bilirubin. Narrowing or damage of bile ductile or bile duct may lead to back flow of bilirubin into the blood stream, filtered in the bowman capsule and hence the excretion of bilirubin through urine. On the other hand, liver damage will also lead to decreased efficiency of bilinogen metabolism and hence increased bilinogen in blood stream and hence in urine.

Blockage of bile duct or bile ductile will lead to obstructive jaundice in which the skin acquires a characteristic yellow appearance due to the backflow of bilirubin into the blood stream and the retention of bilirubin in the blood, that the bilirubin is then filtered in kidney and excreted in urine. Since bilirubin is absence or deficient in digestive tract, the formation of bilinogen will then be substantially reduced or stopped.

Liver is also responsible for the elimination of hemoglobin from the used red blood cells which will lead to the production of bilirubin. When the amount of free bilirubin produced is exceeding the capacity of the liver, the free bilirubin having a low solubility cannot be eliminated in liver and excreted in urine through filtration in kidney. On the other hand, the overload of liver to process the absorbed urine bilinogen will also lead to the increase of bilinogen in urine.

Pancreas disease is another common disease which is susceptible to misdiagnosis, in particularly, acute pancreatitis is a kind of common acute disease of high morality rate. Since the symptom of acute pancreatitis is severe abdominal pain, it is easily to be misdiagnosis in general medical practice. On the other hand, chronic pancreatitis exhibits symptoms of digestive disease which requires pancreas function test for diagnosis.

Internal bleeding of our body is another health hazard which is common but difficult to diagnosis at an early stage or in the asymptomatic period. This is a chronic disease which takes time to develop into a more serious disease, and if diagnosis is made possible during the early stage or the asymptomatic period, the chance of curing of the disease is highly increased.

Calcium imbalance is another common disease. The total calcium of an adult is generally 1 kg which is about 1.5% of the body weight while 99% of the calcium is found in bone. It is difficult to discover calcium imbalance since X-ray analysis can only detect the calcium loss in bone when the calcium level has already been reduced by 30%. While the treatment for calcium loss is simple and effective at the early stage, it is not easy to diagnosis at the early stage.

Urinary tract infection is another common disease, in particularly for married female. It is a chronic disease which is not difficult to cure at its early stage. However, present medical care is still unable to control the medication in according to the real time condition of the patient.

It is shown that a variety of chronic diseases are not hazardous and critical to health if suitable treatment is available and provided at an early stage. Therefore, a medical kit which is easy and convenience to operate, and at the same time, providing a method of use, is capable of promoting self health care and enabling the discovery of a variety of chronic disease at an early stage. Hence, the chance of recovery is highly increased and the development of serious complications is avoided or reduced.

SUMMARY OF THE PRESENT INVENTION

A main object of the present invention is to provide a medical care kit comprising a predetermined plurality of chemical compositions for testing a plurality of predetermined corresponding components in urine.

Another object of the present invention is to provide a medical care kit comprising a predetermined number of testing compositions for testing urine glucose, urine protein, urine bilirubin, urine bilinogen, pancreatic amylase, urine hemoglobin, urine calcium, urine nitrite, urine ketone, and urine pH respectively.

Another object of the present invention is to provide a medical care kit comprising a plurality of chemical compositions for testing urine glucose, urine protein, urine bilirubin, urine bilinogen, pancreatic amylase, urine hemoglobin, urine calcium, urine nitrite, urine ketone, and urine pH wherein the medical care kit employing simple operative procedures is capable of providing preliminary screening tests for a number of diseases, especially chronic diseases, and promoting personal health care.

Another object of the present invention is to provide a medical care kit comprising a predetermined number of testing solutions for testing urine glucose, urine protein, urine bilirubin, urine bilinogen, pancreatic amylase, urine hemoglobin, urine calcium, urine nitrite, urine ketone, and urine pH respectively wherein the medical care kit further comprises an operation manual having principles of operation and operation procedures.

Another object of the present invention is to provide a medical care kit comprising a predetermined composition for medical tests and a method of using the composition which is simple and convenient to use so as to promoting personal health care and increasing the chance of discovering a variety of chronic diseases at its early stage.

Another object of the present invention is to provide a method of personal health care which employs the use of test tube and slide and does not require complicated testing apparatuses and electrical source.

Another object of the present invention is to provide a method of personal health care comprising a predetermined number of medical tests which does not require electrical or complicated testing apparatuses such that the medical tests are capable of carried out as desired and do not restricted by any environmental limitation.

Another object of the present invention is to provide a method of personal health care comprising a predetermined number of medical tests and a predetermined number of spectrum corresponding to the medical tests such that the medical tests are made visualized which is easily to be interpreted.

Another object of the present invention is to provide a method of personal health care comprising a predetermined number of medical tests and a dynamic test records table for recording results of the medical tests.

Another object of the present invention is to provide a method of personal health care comprising a predetermined number of medical tests and a dynamic test records table for recording results of the medical tests such that a health condition of a user is obtained and is capable of being classified as healthy, neutral, or unhealthy.

Accordingly, in order to accomplish the above objects, the present invention is a medical care kit comprising a glucose testing composition, a protein testing composition, a bilirubin testing composition, a bilinogen testing composition, an amylase testing composition, a blood testing composition, a calcium testing composition, a nitrite testing composition, a ketone testing composition and a pH testing composition wherein a preferred testing sample is urine for the medical care kit.

The medical care kit further comprises a plurality of methods of use for the glucose testing composition, the protein testing composition, the bilirubin testing composition, the bilinogen testing composition, the amylase testing composition, the blood testing composition, the calcium testing composition, the nitrite testing composition, the ketone testing composition, and the pH testing composition respectively.

The medical care kit may further comprises a plurality of corresponding indicative spectra to the glucose testing composition, the protein testing composition, the bilirubin testing composition, the bilinogen testing composition, the amylase testing composition, the blood testing composition, the calcium testing composition, the nitrite testing composition, the ketone testing composition, and the pH testing composition respectively such that a health condition of an user is easily be interpreted.

These and other objectives, features, and advantages of the present invention will become apparent from the following detailed description, the accompanying drawings, and the appended claims.

BRIEF DESCRIPTION OF THE DRAWINGS

FIG. 3A illustrates a dynamic testing record diagram of the preferred embodiment of the present invention.

DETAILED DESCRIPTION OF THE PREFERRED EMBODIMENT

Figure 1A:
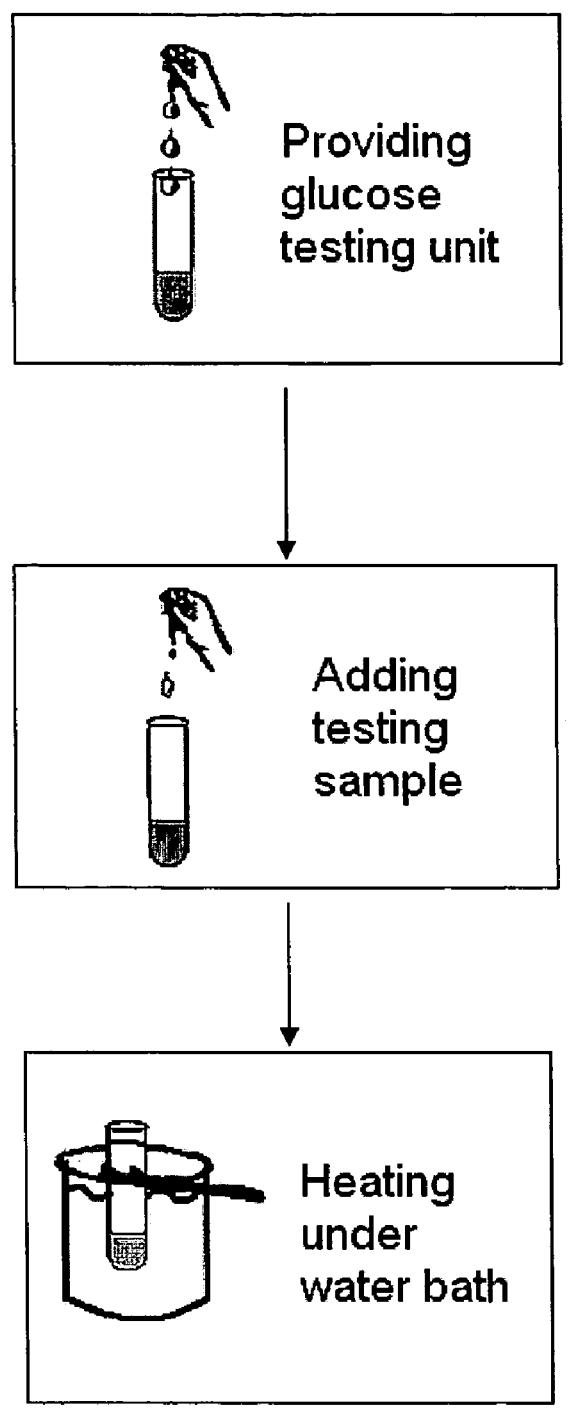
FIGS. 1A to 1J illustrate methods of using testing compositions of the medical care kit of the preferred embodiment of the present invention.

According to the preferred embodiment, the present invention is a medical care kit comprising a glucose testing composition, a protein testing composition, a bilirubin testing composition, a bilinogen testing composition, an amylase testing composition, a blood testing composition, a calcium testing composition, a nitrite testing composition, a ketone testing composition and a pH testing composition.

The preferred embodiment of the present invention further comprises a plurality of predetermined corresponding indicative spectra with respect to the glucose testing composition, the protein testing composition, the bilirubin testing composition, the bilinogen testing composition, the amylase testing composition, the blood indicating composition, the calcium testing composition, the nitrite testing composition, the ketone testing composition and the pH testing composition respectively, wherein each spectrum has a plurality of predetermined color for indicating a result of the corresponding testing composition.

The medical care kit of the present invention also comprises methods of preparing the glucose testing composition, the protein testing composition, the bilirubin testing composition, the bilinogen testing composition, the amylase testing composition, the blood testing composition, the calcium testing composition, the nitrite testing composition, the ketone testing composition and the pH testing composition respectively.

The Glucose Testing Composition

The glucose testing composition has a predetermined composition wherein the composition consists of 9.8-17.3 w/v % sodium citrate, 5.3-10.0 w/v % anhydrous sodium carbonate, 1.5-1.73 w/v % copper sulfate and distilled water, wherein w/v % indicates a weight by volume percentage.

According to the preferred embodiment, the composition of the glucose testing composition consists of 9.8-17.3 g sodium citrate, 5.3-10.0 g anhydrous sodium carbonate, 1.5-1.73 g copper sulfate and a remaining volume of distilled water such that the glucose testing composition is 100 ml in volume.

The method of preparing glucose testing composition as described above comprises the steps of: (a) mixing the sodium citrate and the anhydrous sodium carbonate to form a mixture; (b) adding a first predetermined volume of distilled water and heating the mixture so as to mildly dissolve the mixture in the water to form an intermediate mixture; (c) adding the copper sulfate to the intermediate mixture to form a final mixture which is fully dissolved; and (d) adding a second predetermined volume of distilled water to the final mixture so as to form a final testing solution having a volume of 100 ml.

The final testing solution, which is the preferred embodiment of the glucose testing composition, is a blue solution having a pH 10.7±0.2 and an absorbance 0.15-0.32 A at $\lambda=430$ nm, wherein A is absorbance, $\lambda$ is wavelength and nm is nanometer. The final testing solution can be sealed and stored with a white bottle under room temperature.

The Protein Testing Composition

The protein testing composition has a predetermined composition wherein the composition consists of 9.4-10.5 w/v % salicylic sulfate, 38-50 ml distilled water in 100 ml testing composition, 0.5-2.0 w/v % sodium chloride, 1.0-3.0 v/v % anhydrous acetic acid and 95% methanol, wherein v/v % represents a percentage by volume.

According to the preferred embodiment, the composition of the protein testing composition consists of 9.4-10.5 g salicylic sulfate, 38-50 ml distilled water, 0.5-2.0 g sodium chloride, 1.0-3.0 ml anhydrous acetic acid and a remaining volume of 95% methanol such that the protein testing composition is 100 ml in volume.

The method of preparing the protein testing composition as described above comprises the steps of: (a) mixing the sodium chloride, the anhydrous acetic acid and the distilled water to a completely soluble mixture; (b) adding the salicylic sulfate to the mixture to form a final mixture; (c) shaking the final mixture until the salicylic sulfate is completely soluble in the final mixture; and (d) adding a predetermined volume of 95% methanol so as to form a final testing solution having a volume of 100 ml.

The final testing solution, which is the preferred embodiment of the protein testing composition, is a colorless solution having a pH 1±0.2. The final testing solution can be sealed and stored with a white bottle under room temperature.

The Bilirubin Testing Composition

The bilirubin testing composition has a predetermined composition wherein the composition consists of 0.89-1.2 w/v % acid iron chloride, 20.0-25.3 w/v % acetate chloride, 5.0 ml acetic acid in 100 ml testing composition and distilled water.

According to the preferred embodiment, the composition of the bilirubin testing composition consists of 0.89-1.2 g acid iron chloride, 20.0-25.3 g acetate chloride, 5.0 ml acetic acid and a remaining volume of distilled water such that the bilirubin testing composition is 100 ml in volume.

The method of preparing bilirubin testing composition as described above comprises the steps of: (a) mixing the acetate chloride and the acetic acid until a slightly dissolved mixture is formed; (b) adding the iron chloride to the mixture to form a completely soluble final mixture; and (c) adding a predetermined volume of distilled water to the final mixture so as to form a final testing solution having a volume of 100 ml.

The final testing solution which is the preferred embodiment of the bilirubin testing composition, is a yellowish solution having a pH 10.4±0.2 and an absorbance 0.2-0.6 A at $\lambda$=415 nm. The final testing solution can be sealed and stored in a brown bottle under room temperature.

The Bilinogen Testing Composition

The bilinogen testing composition has a predetermined composition wherein the composition consists of 1.8-2.2 w/v % bimethylbenzaldehyde, 20.0 v/v % concentrated hydrochloric acid, 5.0 v/v % acetic acid and distilled water.

According to the preferred embodiment, the composition of the bilinogen testing composition consists of 1.8-2.2 g bimethylbenzaldehyde, 20.0 ml concentrated hydrochloric acid, 5.0 ml acetic acid and a remaining volume of distilled water such that the bilinogen testing composition is 100 ml in volume.

The method of preparing bilinogen testing composition as described above comprises the steps of: (a) dissolving the bimethylbenzaldehyde completely in the concentrated hydrochloric acid to form a first intermediate mixture; (b) mixing the acetic acid and the distilled water thoroughly to form a second intermediate mixture; and (c) mixing the first and the second intermediate mixture to form a final testing solution. The final testing solution is the preferred embodiment of the bilinogen testing composition having a pH 0.2±0.2 and an absorbance 0.8-1.5 A at $\lambda$=415 nm. The final testing solution can be sealed and stored in a brown bottle under room temperature.

The Amylase Testing Composition

The amylase testing composition has a predetermined composition wherein the composition consists of 0.34 w/v % iodine, 0.68 w/v % potassium iodide, 1 v/v % glycerol and distilled water.

According to the preferred embodiment, the composition of the amylase testing composition consists of 0.34 g iodine, 0.68 g potassium iodide, 1 ml glycerol and a remaining volume of distilled water such that the amylase testing composition is 100 ml in volume.

The method of preparing the amylase testing composition as described above comprises the steps of: (a) dissolving the iodine and the potassium iodide in a first predetermined amount of distilled water; (b) adding the glycerol and shaking to form a final mixture; and (c) mixing a second predetermined amount of distilled water and to the final mixture so as to form a final testing solution having a volume of 100 ml. The final testing solution is the preferred embodiment of the amylase testing composition having a pH 4.85±1.2 and an absorbance 2.0-2.5 A at $\lambda$=480 nm. The final testing solution can be sealed and stored in a brown bottle.

The medical care kit of the present invention may also comprise a supplementary starch solution which has a predetermined composition wherein the composition consists of 0.4 w/v % soluble starch, 1 w/v % sodium chloride, a droplet of chloroform and distilled water. According to the preferred embodiment, the composition of the supplementary starch solution consists of 0.4 g soluble starch, 1 g sodium chloride, a drop of chloroform and a remaining volume of distilled water such that the supplementary starch solution is 100 ml in volume.

The Blood Testing Composition

The blood testing composition has a predetermined composition wherein the composition consists of 0.25-1.0 w/v % benzidine, 40-80 ml acetic acid in 100 ml of testing composition, and 95% methanol. According to the preferred embodiment, the composition of the blood testing composition consists of 0.25-1.0 g benziline, 40-80 ml acetic acid and a remaining volume of 95% methanol such that the blood testing composition is 100 ml in volume.

The method of preparing blood testing composition as described above comprises the steps of: (a) dissolving the benziline in the acetic acid; and (b) adding the 95% methanol to form a final testing solution having a predetermined volume. The final testing solution is the preferred embodiment of the blood testing composition which is a pale brown solution having a pH 1.65±0.3 and an absorbance 0.15-0.55 A at $\lambda$=510 nm. The final testing solution can be sealed and stored in brown bottle.

The medical care kit may further comprise a supplementary blood testing composition having a predetermined composition by weight wherein the composition consists of 8.0-10.0 v/v % 30% hydrogen peroxide solution, 20.0-30.0 v/v % acetic acid and distilled water. According to the preferred embodiment, the composition of the supplementary blood testing composition consists of 8.0 ml 30% hydrogen peroxide solution, 30.0 ml acetic acid and a remaining volume of distilled water such that the supplementary blood testing composition is 100 ml in volume.

The method of preparing the supplementary blood testing composition as described above comprises the steps of: (a) mixing the hydrogen peroxide solution, the acetic acid with a first predetermined volume of distilled water; and (b) adding a second predetermined volume of distilled water so as to form a final supplementary testing solution having a predetermined volume. The final supplementary testing solution is the preferred embodiment of the supplementary blood testing composition which can be sealed and stored in a white bottle under room temperature. The use of protective glove is highly recommended for the preparation method of making the blood testing composition and the supplementary blood testing composition.

The Calcium Testing Composition

The calcium testing composition has a predetermined composition wherein the composition consists of 1.5-2.0 w/v % oxalic acid, 1.5-2.0 w/v % oxalic amide, 3.2-3.5 v/v % acetic acid and distilled water. According to the preferred embodiment, the composition of the calcium testing composition consists of 1.5-2.0 g oxalate, 1.5-2.0 g amine oxalate, 3.2-3.5 ml acetic acid and a remaining volume of distilled water such that the calcium testing composition is 100 ml in volume.

The method of preparing the calcium testing composition as described above comprises the steps of: (a) mixing and dissolving the oxalic acid and the oxalic amide in the acetic acid under a temperature higher than 60° C.; and (b) adding and mixing the distilled water to form a final testing solution having a predetermined volume. The final testing solution is a colorless solution having a pH 2.25±0.25 which can be sealed and stored in while bottle under room temperature.

The Nitrite Testing Composition

The nitrite testing composition has a predetermined composition wherein the composition consists of 0.35-0.45 w/v % sulfanilic acid, 0.2-0.3 w/v % α-naphthyl amide, 1.0-2.0 v/v % methanol, 20-40.0 v/v % acetic acid and distilled water. According to the preferred embodiment, the composition of the nitrite testing composition consists of 0.35-0.45 g sulfanilic acid, 0.2-0.3 g α-naphthyl amide, 1.0-2.0 ml methanol, 20-40.0 ml acetic acid and a remaining volume of distilled water such that the nitrite testing composition is 100 ml in volume.

The method of preparing nitrite testing composition as described above comprises the steps of: (a) dissolving the α-naphthyl amide in the mixture of methanol and acetic acid completely to form a first mixture; (b) dissolving the sulfanilic acid in distilled water under a temperature higher than 60° C. to form a second mixture; and (c) mixing the first and the second mixture and adding the distilled water to form a final testing solution having a predetermined volume.

The Ketone Testing Composition

The ketone testing composition has a predetermined composition by weight wherein the composition consists of 1.24 w/w % sodium nitrofericyanide, 37.04 w/w % anhydrous sodium carbonate, 61.73 w/w % sulfamine. According to the preferred embodiment, the composition of the ketone testing composition consists of 1.24 g sodium nitrofericyanide, 37.04 g anhydrous sodium carbonate, and 61.73 g sulfamine. The total weight of the ketone testing composition is 100 g.

The pH Testing Composition

The pH testing composition has a predetermined composition wherein the composition consists of 0.01 w/v % phenyl red and distilled water. According to the preferred embodiment, the composition of the pH testing composition consists of 0.01 g phenyl red and a remaining volume of distilled water such that the pH testing composition is 100 ml in volume.

The effective ranges of the testing compositions of medical testing kit of the present invention are examined and studied respectively. Methods and results showing the effective ranges of the medical testing kit for each unit are shown as follows:

The Glucose Testing Composition

Simulated glycourine is prepared by dissolving 4 gram glucose with 100 ml distilled water which forms a 4 w/v % glucose solution. Then the simulated glycourine solution is diluted at a 0.5 dilution rate to form a series of simulated glycourine having 8 different concentration levels at: 2 w/v %, 1 w/v %, 0.5 w/v %, 0.25 w/v %, 0.125 w/v %, 0.0625 w/v %, 0.03 w/v %, and 0.015 w/v % respectively.

The glucose test is then carried out using the 8 different concentration levels of the simulated glycourine. Eight test tubes are prepared, each containing 5 ml glucose testing composition and each adding a drop of simulated glycourine having concentration of 2 w/v %, 1 w/v %, 0.5 w/v %, 0.25 w/v %, 0.125 w/v %, 0.0625 w/v %, 0.03 w/v %, 0.015 w/v % respectively. The 8 test-tubes are heated under water bath at 98-100° C. for 5 minutes or microwave the 8 test tubes at a minimum temperature for 10 seconds so as to observe the color change. The results are shown in Table 1 as follows:

| g % | Concentration of simulated glycourine | | | | | | | |
|---|---|---|---|---|---|---|---|---|
| | 2% | 1% | 0.5% | 0.25% | 0.125% | 0.0625% | 0.03% | 0.015% |
| Color | Brownish red | Brownish Yellow | Yellowish Green | Light Yellowish Green | Green | Jade | Bluish Green | Pale Blue |

As shown in Table 1, the glucose testing composition can detect the glucose concentration in the range between 0.03-0.015%.

The Protein Testing Composition

Simulated protein urine has been prepared by completely dissolving 1 gram sodium chloride in distilled water, adding 1 gram fresh albumin, and distilled water to form 100 ml 1 w/v % albumin solution. Afterwards, continuously diluting the albumin solution with a 0.5 dilution rate to form 0.5 w/v %, 0.25 w/v %, 0.125 w/v %, 0.0625 w/v %, 0.03 w/v %, 0.016 w/v %, 0.008 w/v %, 0.004 w/v %, 0.005 w/v % simulated protein urine respectively. Then, the different simulated urine are contained in different test tubes respectively and labeled respectively. Finally, 2-3 drops of protein testing composition are added into the different test tubes for observation. The results are shown in Table 2 as follows:

|  | Concentration of simulated protein urine | | | | | | | | |
|---|---|---|---|---|---|---|---|---|---|
| g % | 0.5% | 0.25% | 0.12% | 0.06% | 0.03% | 0.016% | 0.008% | 0.004% | 0.002% |
| mg/cc | 5 | 2.5 | 1.25 | 0.6 | 0.3 | 0.15 | 0.08 | 0.04 | 0.02 |
| Results | Heavily white precipitation | Obvious white precipitation | Apparent White Precipitation | White Precipitation | Light White Precipitation | Slight White Precipitation | Very slightly white precipitation | Little trace white precipitation | No precipitation |

As shown in Table 2, the protein testing composition can detect the protein concentration in the range between 0.008-0.004%.

The Bilirubin Testing Composition

Simulated bilirubin urine has been prepared by dissolving 2 ml bile with 100 ml distilled water to form 2 v/v % bile solution. Afterwards, continuously diluting the solution with a 0.5 dilution rate to form 1 w/v %, 0.5 w/v %, 0.25 w/v %, 0.125 w/v % simulated bilirubin urine respectively, and pouring into 4 transparent test-tubes, labeling different simulated urine. Finally, adding urine bilirubin solution into 4 test-tubes for observation. The results are shown in Table 3 as follows:

| Unit | Concentration of simulated bilirubin urine | | | |
|---|---|---|---|---|
| ml % | 1 | 0.5 | 0.25 | 0.12 |
| Results | Blue green | Light blue green | Slight blue green | Pale blue green |

As shown in Table 3, the bilirubin testing composition can detect the bilirubin concentration in the range between 0.25-0.125%.

The Bilinogen Testing Composition

Simulated urine bilinogen has been prepared by dissolving sulfonamide with distilled water to form water solution, afterwards, continuously diluting the solution with a 0.5 dilution rate to form 8 mg %, 4 mg %, 2 mg %, 0.25 mg %, 0.125 mg %, 0.06 mg %, simulated urine bilinogen respectively, and then, labeling different simulated urine bilinogen, finally, adding urine bilinogen solution into 4 test-tubes for observation. The results are shown in Table 4 as follows:

|  | Concentration of the simulated urine bilinogen | | | | | | | |
|---|---|---|---|---|---|---|---|---|
| mg % | 8 | 4 | 2 | 1 | 0.5 | 0.25 | 0.12 | 0.06 |
| μl/cc | 80 | 40 | 20 | 10 | 5 | 2.5 | 1.2 | 0.6 |
| Results | Dark Golden | Golden | Light Golden | Yellow | Light Yellow | Pale Yellow | Light pale yellow | trace |

As shown in Table 4, the bilinogen testing composition can detect the bilinogen concentration in the range between 0.25-0.125%.

The Amylase Testing Composition

Simulated urine amylase has been prepared by dissolving 1 gram soluble starch and 1 gram sodium chloride with distilled water to a pasty form, and then, adding 90 ml boiling water to said pasty form, stirring 3 minutes until the solution is clarity, removing heating source, adding 3 drops of chloroform after the temperature decrease below 60° C. (the boiling point of chloroform), mixing evenly, afterwards, adding distilled water to form 100 ml urine amylase solution, then, continuously diluting the solution with a 0.5 dilution rate to form 0.02 w/v %, 0.01 w/v %, 0.005 w/v %, 0.0025 w/v %, 0.00125 w/v %, simulated amylase urine respectively, labeling different simulated urine, adding urine amylase solution into 5 test-tubes for observation. The results are shown in Table 5 as follows:

| Starch Solution (1 ml) | 0.02 w/v % | 0.01 w/v % | 0.005 w/v % | 0.0025 w/v % | 0.00125 w/v % |
|---|---|---|---|---|---|
| Results | Purple | Light Purple | Pale Purple | Light Pale Purple | Colorless |

As shown in Table 5, the amylase testing composition can detect the amylase concentration in the range between 0.25-0.125%.

The Blood Testing Composition

Simulated blood urine has been prepared by dissolving human blood with saline to form urine occult blood solution, and then, continuously diluting the solution with a 0.5 dilution rate to form 0.05%, 0.025%, 0.0125%, 0.006%, 0.003%, 0.0016%, 0.0008% simulated occult blood urine respectively, labeling different simulated urine in different 0.5 ml test-tubes, adding 0.1 ml urine occult blood solution into different test-tubes for observation. The results are shown in Table 6 as follows:

| | Concentration ranges for testing solutions | | | | | | |
|---|---|---|---|---|---|---|---|
| g % | 0.05% | 0.025% | 0.012% | 0.006% | 0.003% | 0.0016% | 0.0008% |
| Results | Dark bluish green | Bluish green | Light bluish green | Slight bluish green | Darker faint bluish green | Faint bluish green | Traced |

As shown in Table 6, the blood testing composition can detect urine blood concentration in the range between 0.003-0.0008%.

The Calcium Testing Composition

Simulated urine calcium has been prepared by continuously diluting the calcium carbonate solution with a 0.5 dilution rate to form 0.2%, 0.1%, 0.05%, 0.025%, 0.012%, 0.006%, 0.003% simulated calcium urine respectively, labeling different simulated urine in different 0.5 ml test-tubes, adding urine calcium solution into different test-tubes for observation. The results are shown in Table 7 as follows:

| | Concentration ranges for testing solution | | | | | | |
|---|---|---|---|---|---|---|---|
| g % | 0.2% | 0.1% | 0.05% | 0.025% | 0.012% | 0.006% | 0.003% |
| Results | Milky precipitate | Tiny white precipitate | White opacity | Light opacity | Slight opacity | Faint opacity | Traced opacity |

As shown in Table 7, the calcium testing composition can detect the calcium concentration in the range between 0.01-0.003%.

The Nitrite Testing Composition

Simultate nitrite urine has been prepared by continuously diluting the nitrite water solution with a 0.5 dilution rate to form 0.005%, 0.0025%, 0.0003%, 0.00016%, 0.00008%, 0.00004%, simulated nitrite urine respectively, labeling different simulated urine in different 0.5 ml test-tubes, adding urine nitrite solution into different test-tubes for observation.

The results are shown in Table 8 as follows:

| | Concentration ranges for testing solutions | | | | | |
|---|---|---|---|---|---|---|
| g % | 0.005 | 0.0025 | 0.0003 | 0.00016 | 0.00008 | 0.00004 |
| Results | Dark cherry-red | Cherry-red | Light cherry-red | Slight cherry-red | Faint cherry-red | Traced |

As shown in Table 8, the nitrite testing composition can detect the nitrite concentration in the range between 00016-0.00008%.

Referring to FIG. 1A to 1J of the drawings, methods of use of the preferred embodiment of the medical testing kit of the present invention are shown. Comparisons of the results obtained from using the medical testing kit and that of the traditional testing method have been studied and examined. It is shown that the results of the medical testing kit of the present invention conform to the results obtained by the traditional testing methods.

The method of use of the glucose testing composition, as shown in FIG. 1A of the drawings, comprises the steps of: (a) providing 0.5 ml glucose testing composition; (b) adding a drop of testing sample to the glucose testing composition; and (c) heating in water bath at 98-100° C. for 5 minutes. The method is used for samples comprising a series of different concentration and the results are shown in Table 1B as follows (M: Results obtained by using the glucose testing composition; and S: Results obtained by using the conventional testing method):

| | Concentration of testing samples | | | | | | | |
|---|---|---|---|---|---|---|---|---|
| g % | 2% | 1% | 0.5% | 0.25% | 0.125% | 0.0625% | 0.03% | 0.015% |
| M | Brown red | Brown yellow | Yellowish green | Light yellowish green | Green | Emerald green | Bluish green | Light blue |
| S | ++++ | +++ | ++ | ++ | + | + | ± | ± |

It is thus clearly shown that the results obtained from the glucose testing composition and that obtained from the conventional testing method are identical, and the glucose testing composition of the present invention is at least as effective as the conventional testing method having at least the same effective range as the conventional testing method.

Figure 1B:
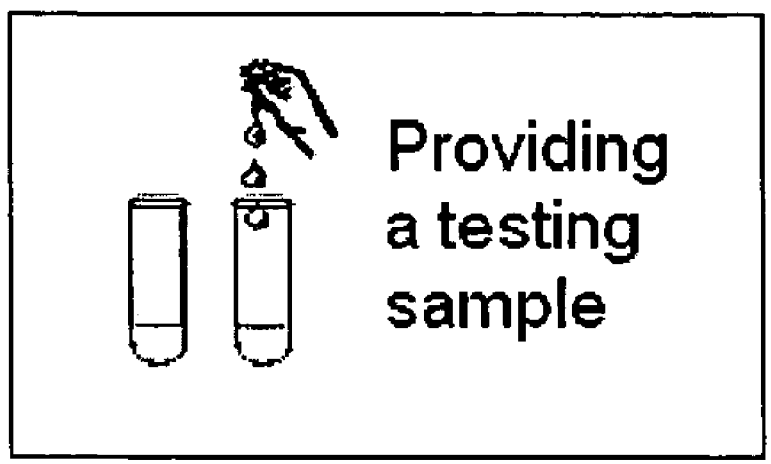
Figure 1B:
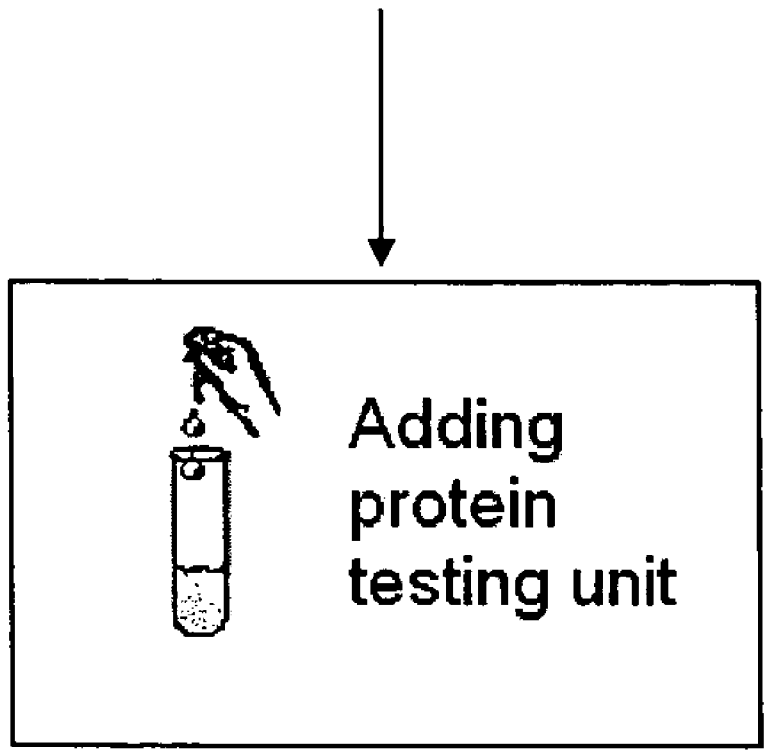

The method of use of the protein testing composition, as shown in FIG. 1B of the drawings, comprises the steps of (a) providing 0.5 ml testing sample; (b) adding 2 drops of the protein testing composition to the testing sample; and (c) observing the result. The method is used for testing samples comprising a series of different concentration and the results are shown in Table 2B as follows (M: Results obtained by using the protein testing composition; and S: Results obtained by using the conventional testing method):

| | Concentration of testing samples | | | | | | | | |
|---|---|---|---|---|---|---|---|---|---|
| g % | 0.5% | 0.25% | 0.12% | 0.06% | 0.03% | 0.016% | 0.008% | 0.004% | 0.002% |
| mg/cc | 5 | 2.5 | 1.25 | 0.6 | 0.3 | 0.15 | 0.08 | 0.04 | 0.02 |
| M | Opacified mass precipitate | Opacified flocculent precipitate | Milky turbidity | White turbidity | Light White turbidity | slight turbidity | Faint turbidity | Traced turbidity | No turbidity |
| S | ++++ | +++ | ++ | ++ | + | + | ± | ± | − |

It is thus clearly shown that the results obtained from the protein testing composition and that obtained from the conventional testing method are identical, and the protein testing composition of the present invention is at least as effective as the conventional testing method having at least the same effective range as the conventional testing method.

Figure 1C:
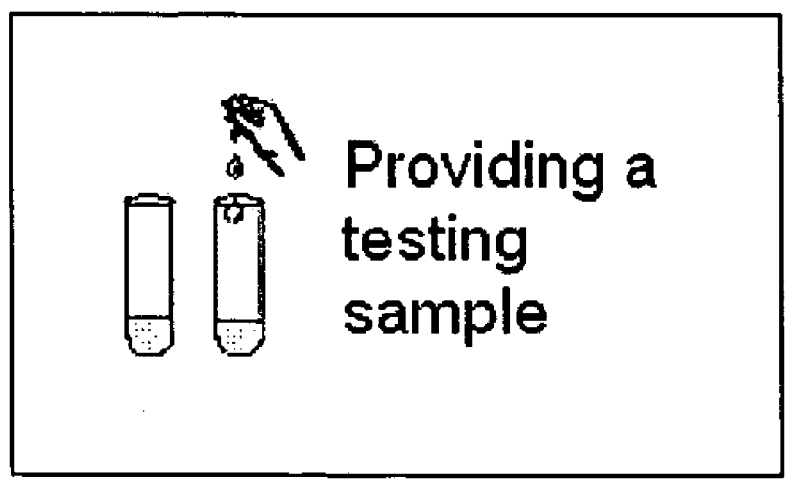
Figure 1C:
Figure 1C:
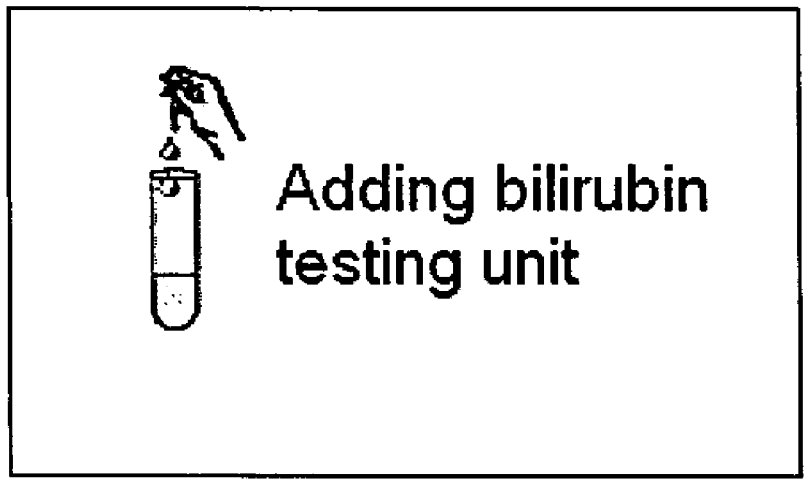

The method of use of the bilirubin testing composition, as shown in FIG. 1C of the drawings, comprises the steps of (a) providing 10 drops of testing sample; and (b) adding 2 drops of the bilirubin testing composition to the testing sample and observing the result. The method is used for testing samples comprising a series of different concentration and the results are shown in Table 3B as follows (M: Results obtained by using the protein testing composition; and S: Results obtained by using the conventional testing method):

| | Concentration of testing samples | | | |
|---|---|---|---|---|
| | 1% | 0.5% | 0.25% | 0.12% |
| M | Bluish green | Light bluish green | Slight bluish green | Faint bluish green |
| S | ++++ | +++ | ++ | + |

It is thus clearly shown that the results obtained from the bilirubin testing composition and that obtained from the conventional testing method are identical, and the bilirubin testing composition of the present invention is at least as effective as the conventional testing method having at least the same effective range as the conventional testing method.

Figure 1D:
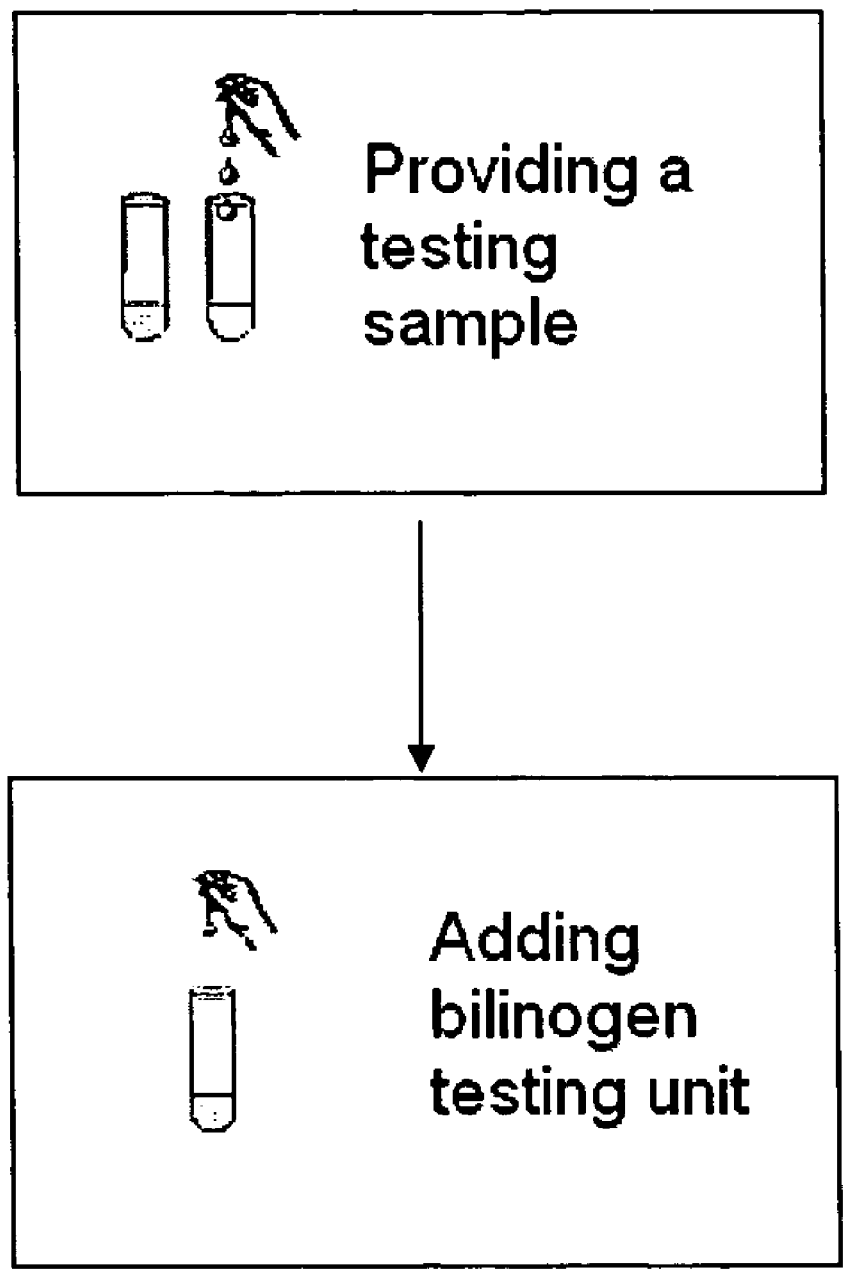

The method of use of the bilinogen testing composition, as shown in FIG. 1D of the drawings, comprises the steps of (a) providing a 0.5 ml testing sample; and (b) adding 2 drops of the bilinogen testing composition and observing the color. The method is used for testing samples comprising different concentration and the results are shown in Table 4B as follows (M: Results obtained by using the protein testing composition; and S: Results obtained by using the conventional testing method):

| | Concentration of testing samples | | |
|---|---|---|---|
| | >1/20 | <1/20 | 0 |
| M | Cherry-red | Light red | Original color |
| S | Strong positive | positive (Normal) | Negative (Abnormal) |

It is thus clearly shown that the results obtained from the bilinogen testing composition and that obtained from the conventional testing method are identical, and the bilinogen testing composition of the present invention is at least as effective as the conventional testing method having at least the same effective range as the conventional testing method.

Figure 1E:
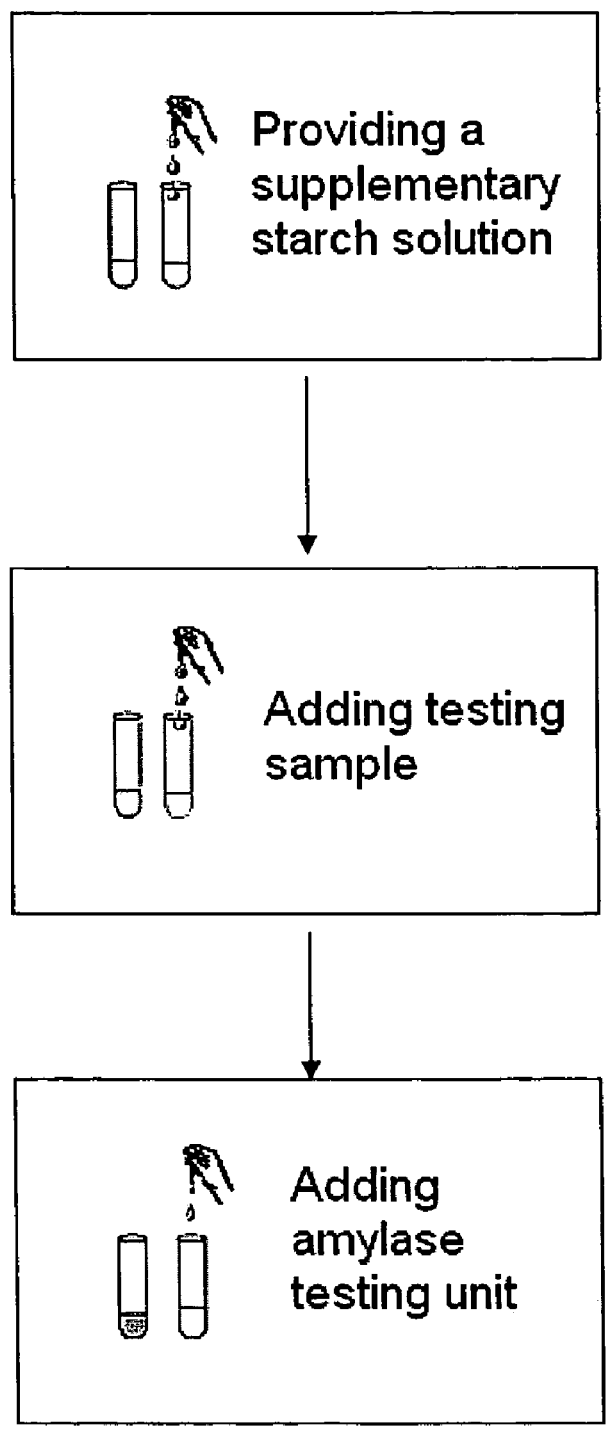

The method of use of the amylase testing composition, as shown in FIG. 1E of the drawings, comprises the steps of: (a) providing a supplementary starch solution; (b) adding a standardized testing sample to the supplementary solution; and (c) adding the amylase testing composition and observing the result. The method is used for testing samples comprising different concentrations in Wentworth Unit (U) and the results are shown in Table 5B as follows:

| 8U | 16U | 32U | 64U | 128U | Indication |
|---|---|---|---|---|---|
| colorless | Purple or colorless | Purple or colorless | Purple | Purple | normal |
| Purple | Purple | Purple | Purple | Purple | Inferior function |
| colorless | colorless | colorless | colorless | colorless | Hyper-function |

The standardized testing samples comprising different concentration in Wentworth Unit (U) have been prepared according to Table 5B' as follows:

| | U | | | | |
|---|---|---|---|---|---|
| | 8 U | 16 U | 32 U | 64 U | 128 U |
| Supplementary Starch Solution (No. of drop) | 10 | 8 | 16 | 16 | 32 |
| Testing sample (No. of drop) | 5 | 2 | 2 | 1 | 1 |

It is thus clearly shown that the results obtained from the amylase testing composition and that obtained from the conventional testing method are identical, and the amylase testing composition of the present invention is at least as effective as the conventional testing method having at least the same effective range as the conventional testing method.

Figure 1F:
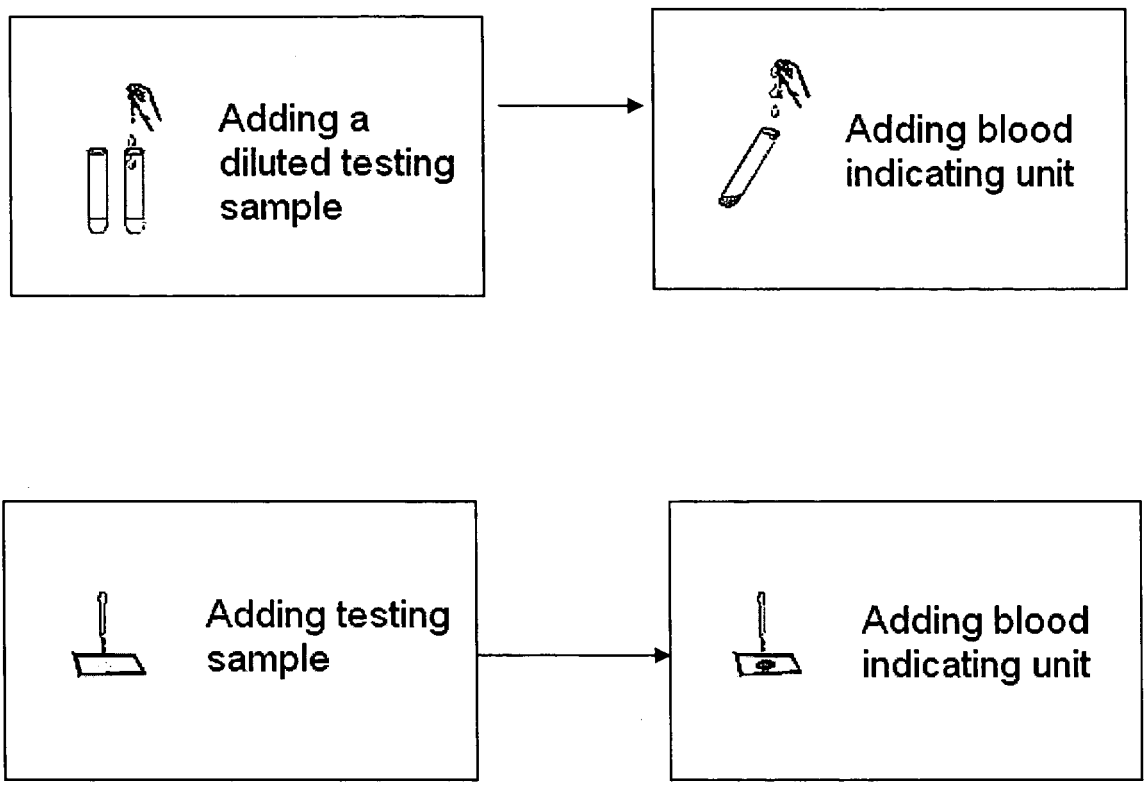

The first method of use of the blood testing composition, as shown in FIG. 1F of the drawings, comprises the steps of (a) providing a predetermined amount of testing sample wherein the amount is 10 drops; and (b) adding 2 drops of the blood testing composition and 2 drops of the supplementary blood testing composition.

An alternate method of use of the blood testing composition may be provided wherein the step (a) is replaced by a step (a') providing a diluted testing sample wherein the diluted testing sample is prepared by mixing 2 drops of testing sample and 10 drops of diluting solution.

The second method of use of the blood testing composition, as shown in FIG. 11F of the drawings, comprises the steps of (a) providing a testing sample; and (b) adding one drop of the blood testing composition and one drops of the supplementary blood testing composition. The testing sample of the second method may be in solid or liquid forms such as urine, feces or salvia.

Accordingly to the results obtained by using the blood testing composition, the results: dark bluish green (++++), bluish green (+++), light bluish green (++), slight bluish green (+), faint bluish green (±) and trace (±) are the same as that of the conventional testing method.

Figure 1G:
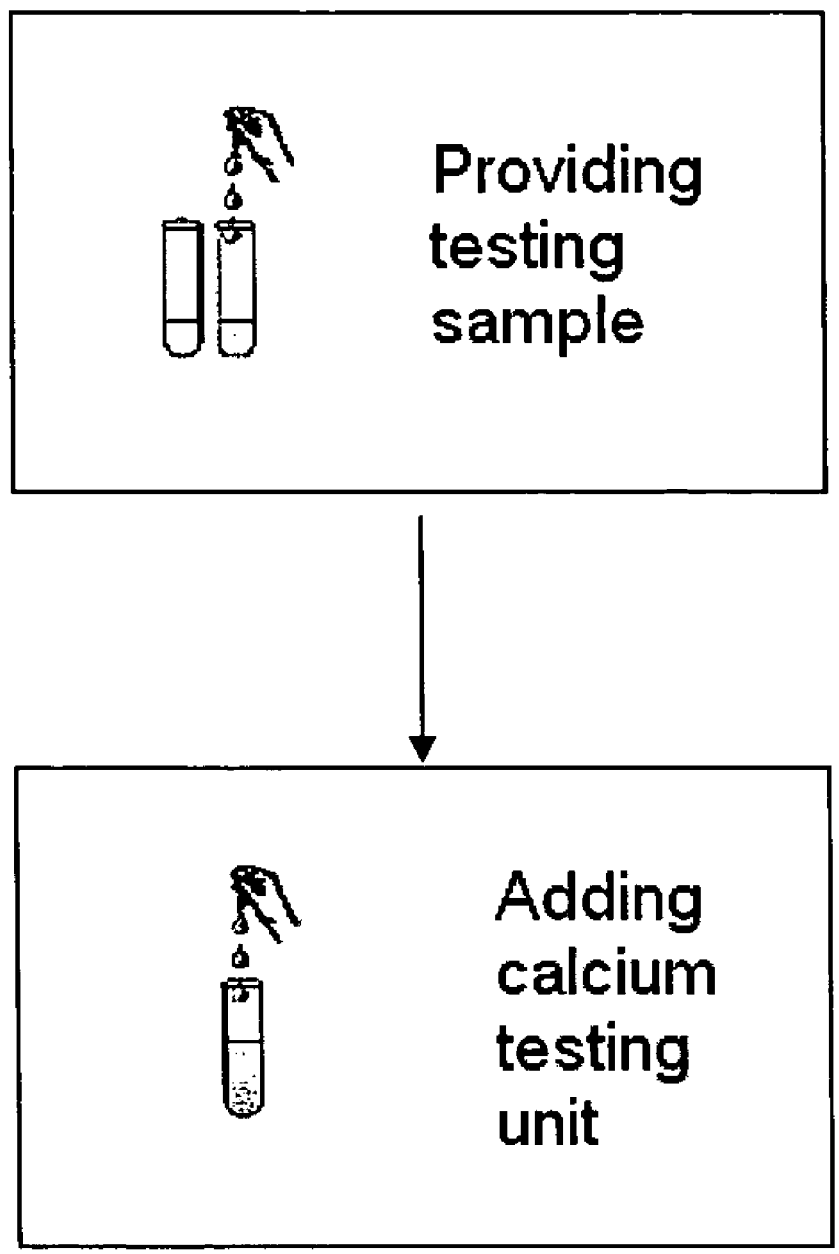

The method of use of the calcium testing composition, as shown in FIG. 1G of the drawings, comprises the steps of (a) providing 10 drops of testing sample; and (b) adding 10 drops of the calcium testing composition to the test sample. The testing sample is urine obtained from a 24 hours period or two 12 hours period. The method is used for testing samples comprising a series of different concentration and the results are shown in Table 7B as follows (M: Results obtained by using the protein testing composition; and S: Results obtained by using the conventional testing method):

| | Concentration of testing samples | | | | | | |
|---|---|---|---|---|---|---|---|
| g % | 0.2% | 0.1% | 0.05% | 0.025% | 0.012% | 0.006% | 0.003% |
| M | Milky precipitate | Tiny white precipitate | White opacity | Light opacity | Slight opacity | Tint opacity | Trace |
| S | ++++ | +++ | ++ | + | + | − | − |

The method further comprises a step (c) placing a text paper as a background for observing the results. Results showing enlarged and clear text indicated the reduced urine calcium (0.006-0.003%); blurred text indicated normal urine calcium(0.025-0.012%); indistinct text indicated the increased urine calcium(0.2-0.05%). Accordingly, results showed that and the calcium testing composition of the present invention is at least as effective as the conventional testing method having at least the same effective range as the conventional testing method.

Figure 1H:
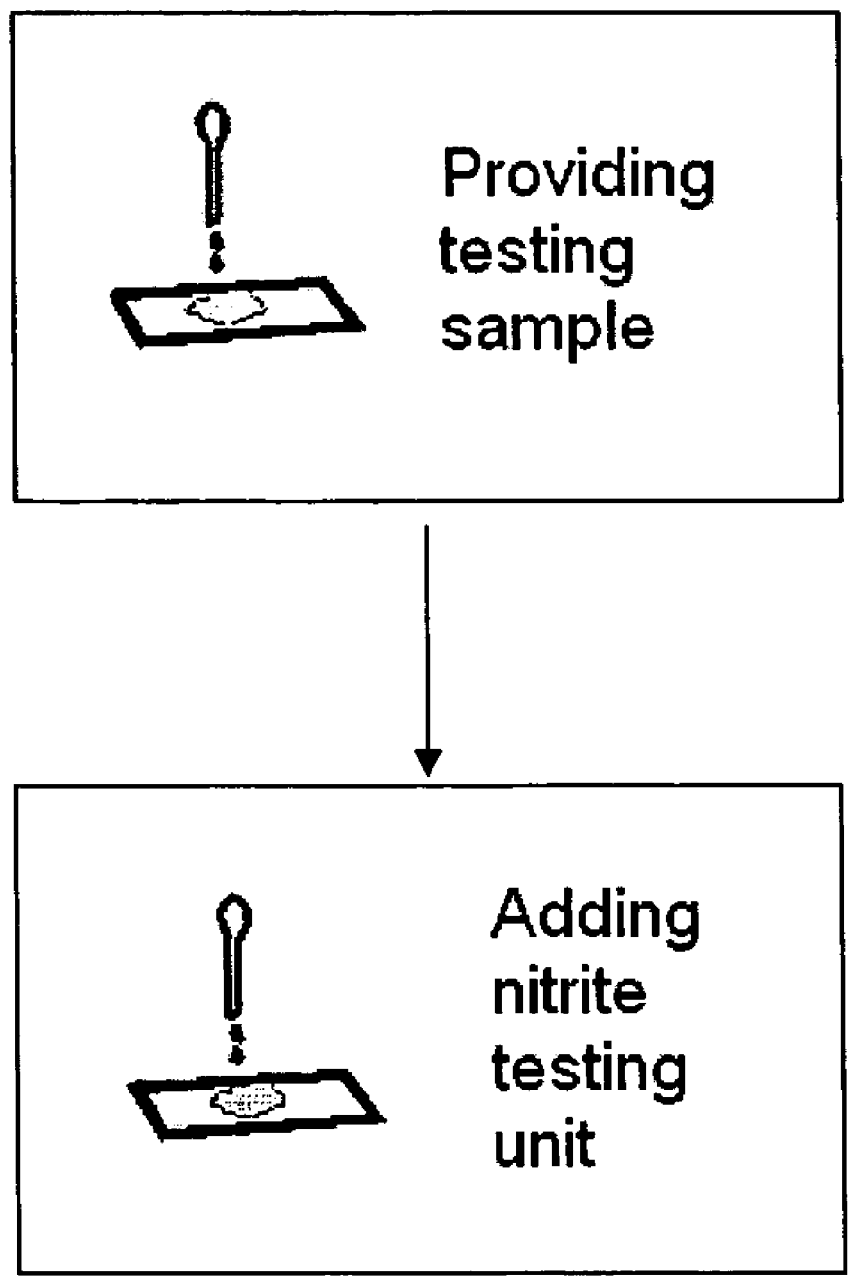

The method of use of the nitrite testing composition, as shown in FIG. 1H of the drawings, comprises the steps of (a) providing one drop of testing sample; and (b) providing one drop of the nitrite testing composition. The method is used for testing samples comprising a series of different concentration and the results are shown in Table 8B as follows (M: Results obtained by using the protein testing composition; and S: Results obtained by using the conventional testing method):

| | Concentration ranges of testing result | | | | | |
|---|---|---|---|---|---|---|
| g % | 0.005 | 0.0025 | 0.0003 | 0.00016 | 0.00008 | 0.00004 |
| M | Dark cherry-red | Cherry-red | Light cherry-red | Slight pinked red | Faint pinked red | trace |
| S | ++++ | +++ | ++ | + | + | ± |

It is thus clearly shown that the results obtained from the nitrite testing composition and that obtained from the conventional testing method are identical, and the nitrite testing composition of the present invention is at least as effective as the conventional testing method having at least the same effective range as the conventional testing method.

Figure 1I:
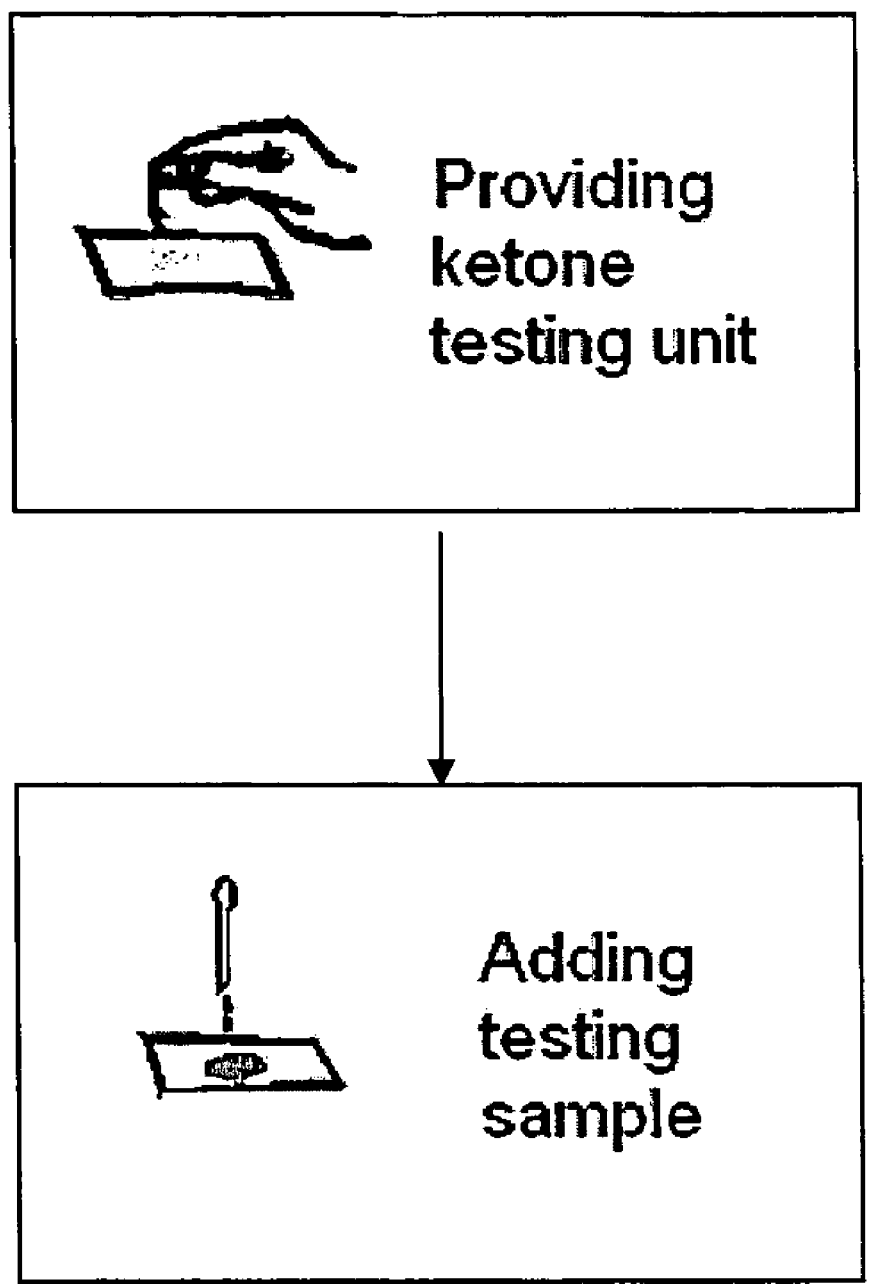

The method of use of the ketone testing composition, as shown in FIG. 1I of the drawings, comprises the steps of (a) providing a testing sample; and (b) adding the ketone testing composition to the testing sample. The presence of ketone in the testing sample is shown by the presence of pale red and purple red color.

Figure 1J:
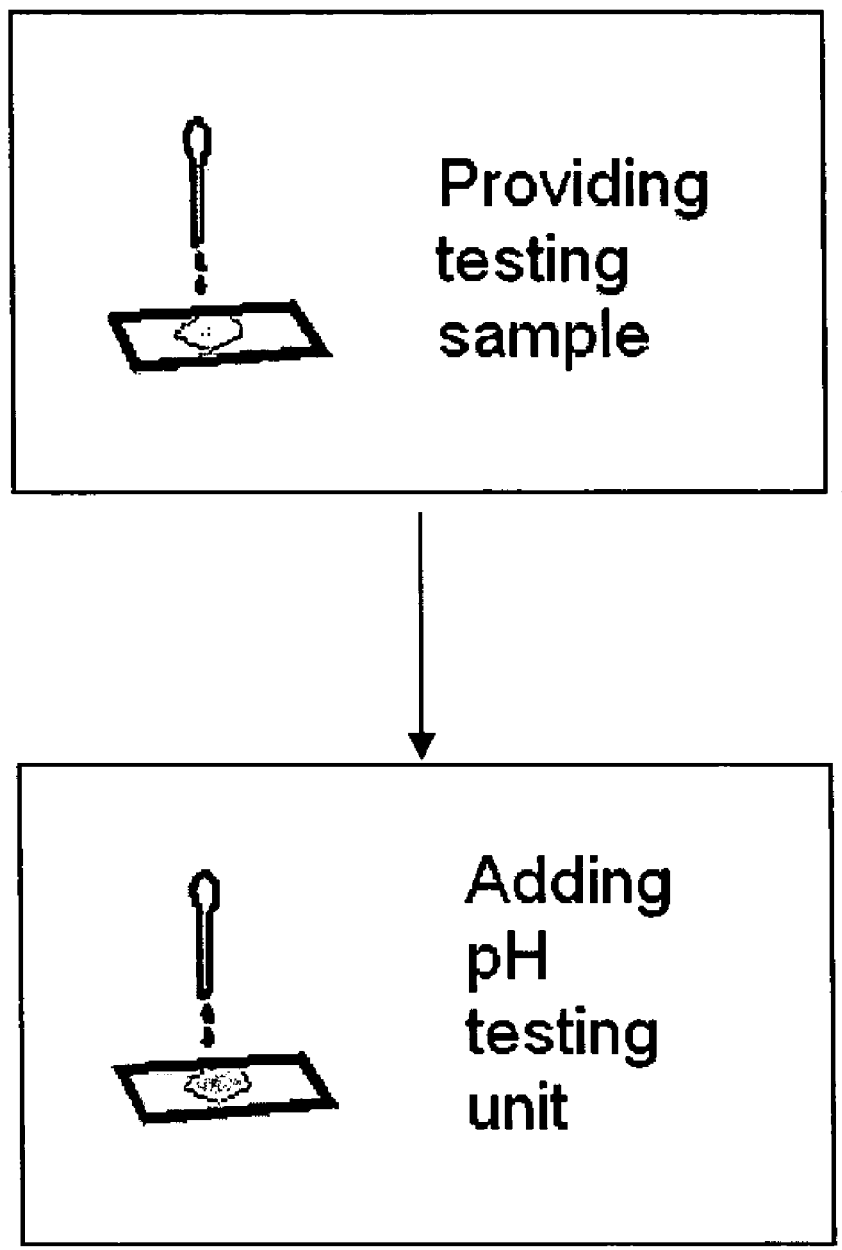

The method of use of the pH testing composition, as shown in FIG. 1J of the drawings, comprises the steps of (a) providing a testing sample; and (b) adding the pH testing composition to the testing sample. The quantity of the testing sample and the pH testing composition is in the ratio of 1:1. According to the natural of the testing sample, that is, alkaline, neutral, and acidic, the color, red, orange and yellow will be shown respectively.

Figure 2:
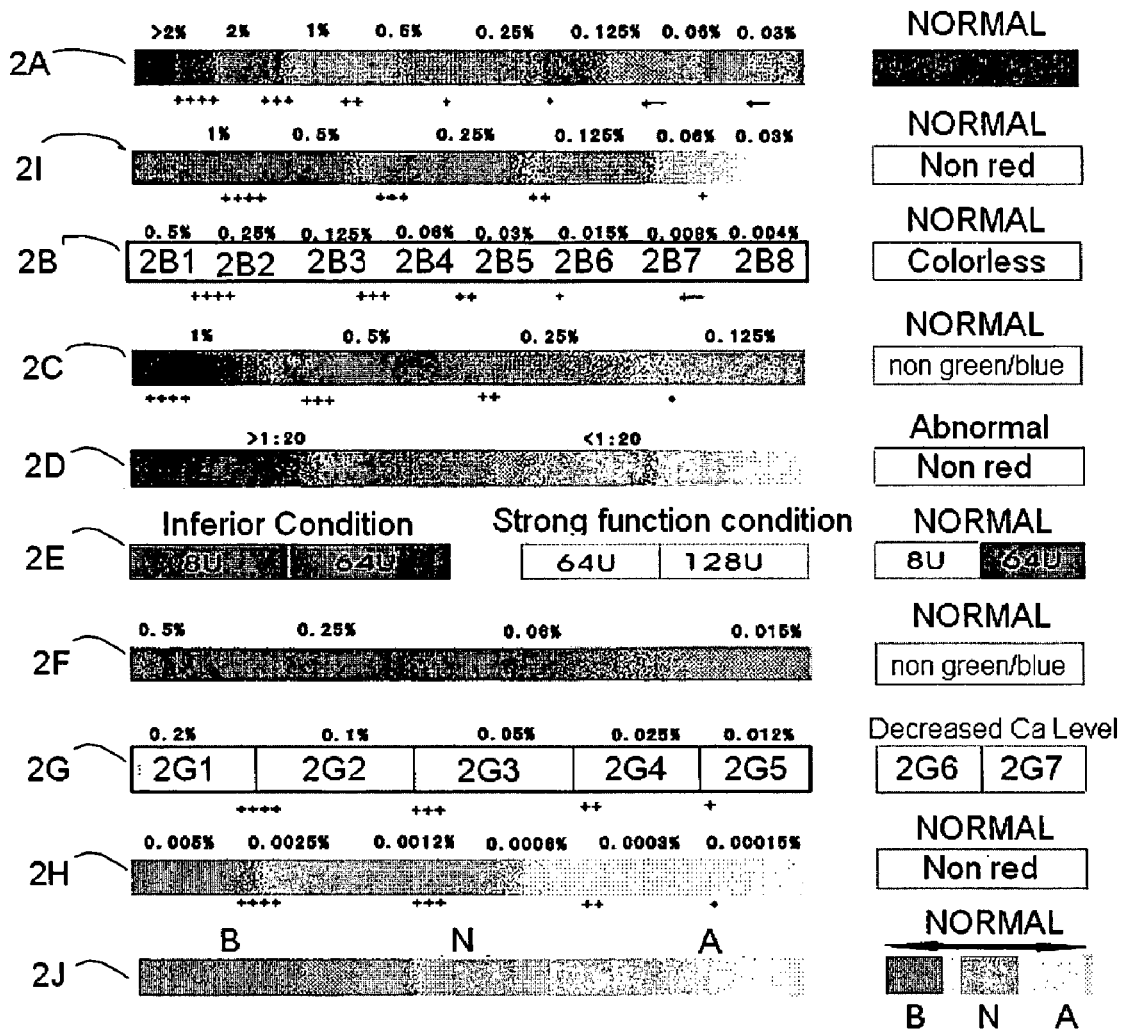
FIG. 2 illustrates a predetermined number of quantitative spectra for the testing compositions of the preferred embodiment of the present invention.

Referring to FIG. 2 of the drawings, quantitative spectra of glucose, ketone, protein, bilirubin, bilinogen, amylase, blood, calcium, nitrous salt, and pH of the preferred embodiment of the present invention are shown respectively. The quantitative spectra are prepared in according to a predetermined range of results for the glucose testing composition, the ketone testing composition, the protein testing composition, the bilirubin testing composition, the bilinogen testing composition, the amylase testing composition, the blood testing composition, the calcium testing composition, the nitrite testing composition, and the pH testing composition respectively such that only a simple comparison is required for quantifying and interpreting the results of the testing compositions of the medical testing kit. Fresh urine is the preferred testing sample.

As shown in FIG. 2 of the drawings, the spectrum for glucose testing composition 2A comprises the color change from light blue, bluish green, yellowish green, yellowish brown, and brick red in according to the change of glucose concentration from 0.03% to 2% or higher percentage. In addition, the corresponding standard indication of the conventional method are also shown with respect to the spectrum. A testing result of blue color indicates a normal condition.

As shown in FIG. 2 of the drawings, the spectrum for the protein testing composition 2B comprises the range of opacified mass precipitate 2B1, opacified flocculent precipitate 2B2, obvious white turbidity 2B3, white turbidity 2B4, light turbidity 2B5, slight turbidity 2B6, faint turbidity 2B7, traced turbidity 2B8 with respect to the protein concentration of 5 mg/cc, 2.5 mg/cc, 1.25 mg/cc, 0.6 mg/cc, 0.3 mg/cc, 0.15 mg/cc, 0.08 mg/cc, 0.04 mg/cc respectively. In addition, the corresponding standard indications of the conventional method are also shown with respect to the spectrum. A colorless result indicates a normal condition.

As shown in FIG. 2 of the drawings, the spectrum for the bilirubin testing composition 2C comprises the color bluish green, light bluish green, slight bluish green, and faint bluish green corresponding to the bilirubin concentration at 1%, 0.5%, 0.25%, and 0.12% respectively. The spectrum is capable of indicating the color corresponding to the concentration. In addition, the corresponding standard indication of the conventional method is also shown with respect to the spectrum. A non-green and non-blue result indicates a normal condition.

As shown in FIG. 2 of the drawings, the spectrum for the bilinogen testing composition 2D comprises the color cherry red and light red corresponding to the bilinogen concentration lower than 1/20 (normal) and higher than 1/20 (abnormal) respectively. The spectrum is capable of indicating the color corresponding to the concentration. A non red result indicates an abnormal condition.

As shown in FIG. 2 of the drawings, the spectrum for the amylase testing composition 2E is shown wherein a purple color of 8 U testing sample indicates an inferior pancreas function condition; a colorless color of 64 U sample indicates a strong function pancreas condition. Different concentrations of testing sample in Wentworth Unit are used for providing different reference color for testing and contrasting test results. A 8 U colorless and 64 U purple result indicates a normal condition.

As shown in FIG. 2 of the drawings, the spectrum for the blood testing composition 2F comprises the color change between dark bluish green, bluish green, light bluish green, slight bluish green, bright faint bluish green and faint bluish green according to the amylase concentration of 0.05%, 0.025%, 0.012%, 0.006%, 0.003%, and 0.0016% and 0.0008% respectively. A non-green and non-blue result indicates a normal condition.

As shown in FIG. 2 of the drawings, the spectrum for the calcium testing composition 2G comprises the results of milky precipitate 2G1, tiny white precipitate 2G2, white opacity 2G3, light opacity 2G4, slight opacity 2G5, faint opacity 2G6, and traced opacity 2G7 with respect to the calcium concentration of 0.2%, 0.1%, 0.05%, 0.025%, 0.012%, 0.006% and 0.003% respectively. The spectrum is capable of indicating the color in response to the concentration. In addition, the corresponding standard indications of the conventional method are also shown with respect to the spectrum. A faint opacity 2G6 or a traced opacity 2G7 indicates a decreased calcium level which requires attention.

As shown in FIG. 2 of the drawings, the spectrum for the nitrite testing composition 2H comprises the results of dark cherry-red, cherry-red, light cherry-red, slight cherry-red, faint cherry-red, and traced cherry-red with respect to the nitrite concentration of 0.005%, 0.0025%, 0.0003%, 0.00015%, 0.00008%, and 0.00004% respectively. The spectrum is capable of indicating the color in response to the concentration. In addition, the corresponding standard indications of the conventional method are also shown with respect to the spectrum. A non-red result indicates a normal health condition.

Referring to FIG. 2 of the drawings, the spectrum for the ketone testing composition 21 comprises the color change between different level of redness corresponding to the ketone concentration between 0.03% and 1% or higher are shown respectively. The spectrum is capable of indicating the color corresponding to the concentration. A non-red result indicates a normal condition.

Referring to FIG. 2 of the drawings, the spectrum for the pH testing composition 2J is shown, which is identical to the universal pH standard. Alkalinity B, neutral N, and acidic A are classified according to the color of the spectrum for the pH testing composition 2J.

According to the method of use of the medical test kit of the present invention, the preferred testing sample used are urine freshly obtained from a user. The standard of 'one' drop is equal to 0.05±0.005 ml. A dropper may be used for dropping purpose, and the preferred dropper is 1 ml in volume having a total of 20±2 drops.

Figure 3A:
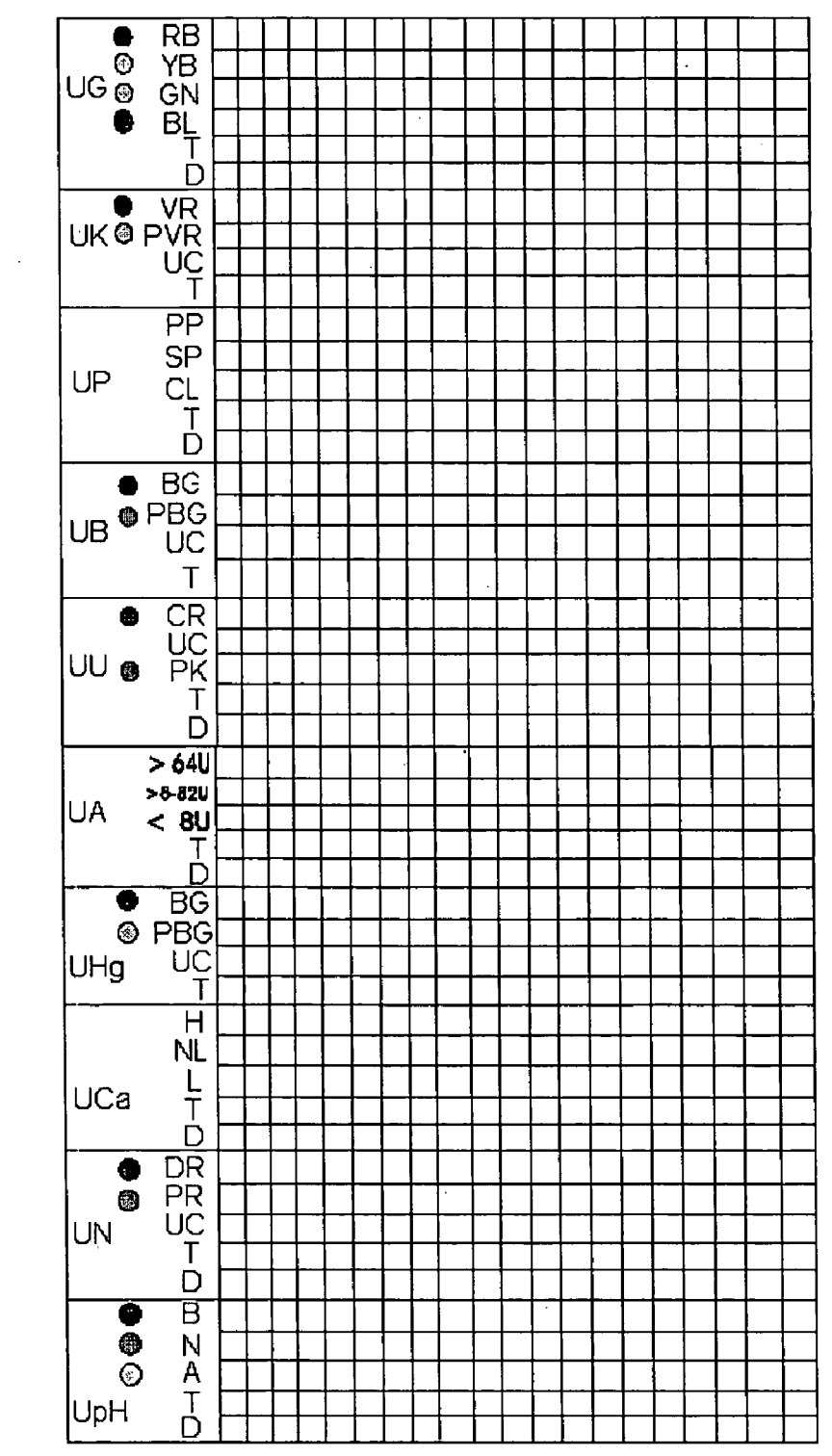
Figure 3B:
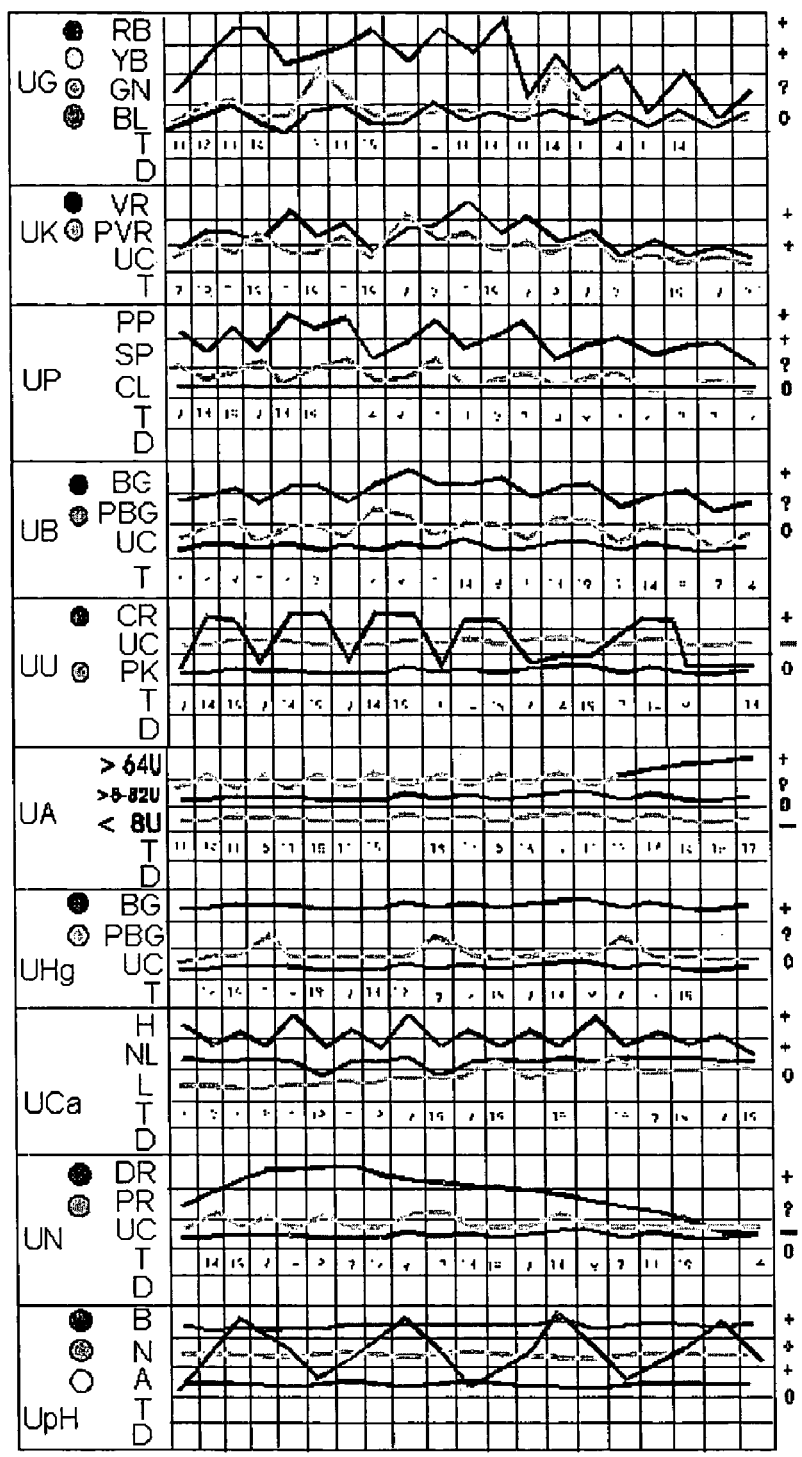
FIG. 3B illustrates a dynamic testing record diagram having testing records of a healthy user of the preferred embodiment of the present invention.

Referring to FIGS. 3A and 3B of the drawings, the dynamic testing record diagram of the preferred embodiment of the present invention and an illustrative example of the dynamic testing record diagram of a healthy user are shown. The diagram comprises 10 sections, namely, urine glucose (UG), urine ketone (UK), urine protein (UP), urine bilirubin (UB), urine bilinogen (UU), urine amylase (UA), urine occult blood (UHg), urine calcium (UCa), urine nitrite (UN), and urine pH (UpH).

Referring to FIGS. 3A and 3B of the drawings, RB represents red brown, YB represents yellow brown, GN represents green, BL represents blue, T represents time, D represents date, VR represents violet red, PVR represents pale violet red, UC represents urine color, PP represents settled precipitate, SP represents suspended precipitate, CL represents clear, BG represents blue green, PBG represents pale blue green, CR represents cherry red, PK represents pink, H represents high, NL represents normal, L represents low, DR represents deep red, PR represents pale red, B represents alkaline, N represents neutral, and A represents acidic.

Referring to FIG. 3A of the drawings, each section of the dynamic testing record diagram of the preferred embodiment of the present invention comprises a plurality of predetermined sub-sections at least comprising a time section (T) and a date section (D) for recordation of time and date, and a predetermined result subsection categorizing results of the testing compositions of the medical test kit.

1. Urine glucose is capable of representing sugar metabolism. Since there are individual differences of sugar metabolism and pathological controlling, a complete and cyclic dynamic-tracing testing is necessary to diagnosis the terminating process of sugar metabolism. According the preferred embodiment of present invention, the user can record continuous testing results, represented by different color dots, in the recording sheet. Afterwards, the color dots are linked into a curved indicating line to form a dynamic graphic chart. The color red-brown (RB), yellow brown (YB), green (GN), blue (BL) are used in the illustrative diagram as shown in FIGS. 3A and 3B.

Based on the chart, the user is capable of obtaining a precise and update information such as whether he suffers diabetes, which type of diabetes he is suffering, cause of diabetes, etc. As a result, the early detectable rate of diabetes can be dramatically increased and contemporary monitoring is enforced.

For instance, if blood sugar exceeds 160 mg % renal threshold, it may indicate the diabetes I or diabetes II caused by glucose filtration and reabsorbing of glomerular. Instead, a renal threshold below 160 mg/%, an inferior function of glomerular absorption is highly possible.

2. Urine ketone is an indicator for ketone, which is crucial indicator for kidney function, and is an indirect indicator for glucose level. It is crucial to detect early ketoacidosis. The color violet red (VR) and pale violet red (PVR) are used in the illustrative diagram as shown in FIGS. 3A and 3B.

3. Urine protein is an indicator for kidney function. The serially tested urine protein results are represented by different reactive colors from the time to time testing intervals. According to the preferred embodiment of present invention, the user can record continuous testing results, represented by different color dots, in the recording sheet. Afterwards, the color dots are linked into a curved indicating line to form a dynamic graphic chart.

Based on the urine protein dynamic graphic chart, the user is then able to obtain a precise and update information such as whether he is suffering nephropathy or overall nephropathy complications, and causes of nephropathy, etc. As a result, the early detectable rate of nephropathy is dramatically increased and contemporary monitoring of nephropathy is enforced.

4. Urine bilirubin and urine bilinogen are indicators for liver function. According to periodic rule of urine bilirubin and bilinogen metabolism, different reactive color dots, representing continuous testing results in different periods, can be filled into a urine bilirubin and bilinogen dynamic graphic chart.

Based on the urine bilirubin and bilinogen dynamic graphic chart, the user is able to obtain a precise and update information such as whether he is suffering hepatic illness, and the causes of hepatic illness, etc. As a result, the early detectable rate of nephropathy is dramatically increased and contemporary monitoring of hepatic illness is enforced.

5. Urine amylase is an indicator for pancreatic function. According to rules of amylase, different reactive color dots, representing continuous testing results in different periods, can be filled into a urine amylase dynamic graphic chart.

The assistant information is indicated on the chart. For instance, normal pancreas amylase activity of health pancreas is within the range from 8 U to 32 U (Wentworth unit). Generally, there is a colorless reaction in 8 U test-tube, while the Wentworth unit equals to or bigger than 32 U is supposed to be colored reacted. On the other hand, if the 8 U test-tube is shown purple color, it indicates an incomplete starch decomposition which represents an inferior pancreas function. In case the 64 U test-tube is colorless, over activity of pancreas is highly possible due to the fact that excessive starch may be decomposed by amylase. Under this circumstance, the 128 U test-tube is employed immediately to check the acute pancreasititis. If the 128 U test-tube is still colorless, going to a doctor is required.

6. Urine occult blood is an indicator for internal bleeding. According to the nature of organic micro hemorrhage, a dynamic tracing testing is absolutely necessary. And different reactive color dots, representing continuous testing results in different periods, can be filled into a urine occult blood dynamic graphic chart.

Based on the urine occult blood dynamic graphic chart, the user is able to obtain a precise and update information such as whether he is suffering organic micro hemorrhage, portion of hemorrhage, causes of hemorrhage, etc. As a result, the early detectable rate of micro organic hemorrhage is dramatically increased and contemporary monitoring of micro organic hemorrhage is enforced.

7. Urine calcium is an indicator for calcium metabolism: Since there are existing huge individual differences of calcium metabolism and pathological controlling, a complete, cyclic dynamic tracing testing is necessary to diagnosis the terminating-process of calcium metabolism. According the preferred embodiment of present invention, the user could record continuous testing results, represented by different color dots, in the recording sheet. Afterwards, the color dots could be linked into a curved indicating line to form a urine calcium dynamic graphic chart.

Based on the urine calcium dynamic graphic chart, the user is able to obtain a precise and update information such as whether he is suffering unbalanced calcium metabolism, and causes of hemorrhage, etc. As a result, the early detectable rate of unbalanced calcium metabolism is dramatically increased and contemporary monitoring of insufficient calcium intake and endocrine dyscrasia is enforced.

8. Urine nitrite is an indicator for urinary tract infection. The user can be filled in the recording sheet with different colors representing continuously tested results, and then, link the results with a curved line to form a urine nitrite dynamic graphic chart.

Based on the urine nitrite dynamic graphic chart, the user is then able to obtain a precise and update information to enforce contemporary monitoring of urine tract infection.

9. Urine pH is an indicator for screening the health condition of a user. Any irregularities can give us an alert for further testing.

Figure 4:
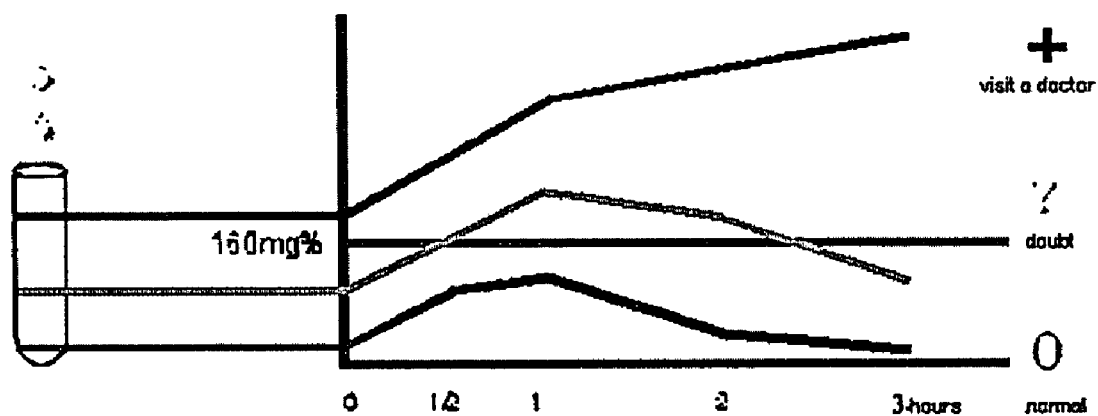
FIG. 4 illustrates a section of the dynamic testing record diagram which shows the interpretation method for the dynamic testing record diagram.

Referring to FIG. 4 of the drawings, a section of the dynamic testing record diagram which illustrates the interpretation method for the dynamic testing record diagram is shown. A curve indicating a condition having higher than value than a predetermined threshold value in a '+' zone suggests that further visit to a doctor is required, a curve indicating a condition having an average value closed to the threshold value in a '?' zone suggest doubt on the health condition of the user, while a curve indicating a condition below the threshold in a '0' zone suggests that the health condition is good.

Figure 5:
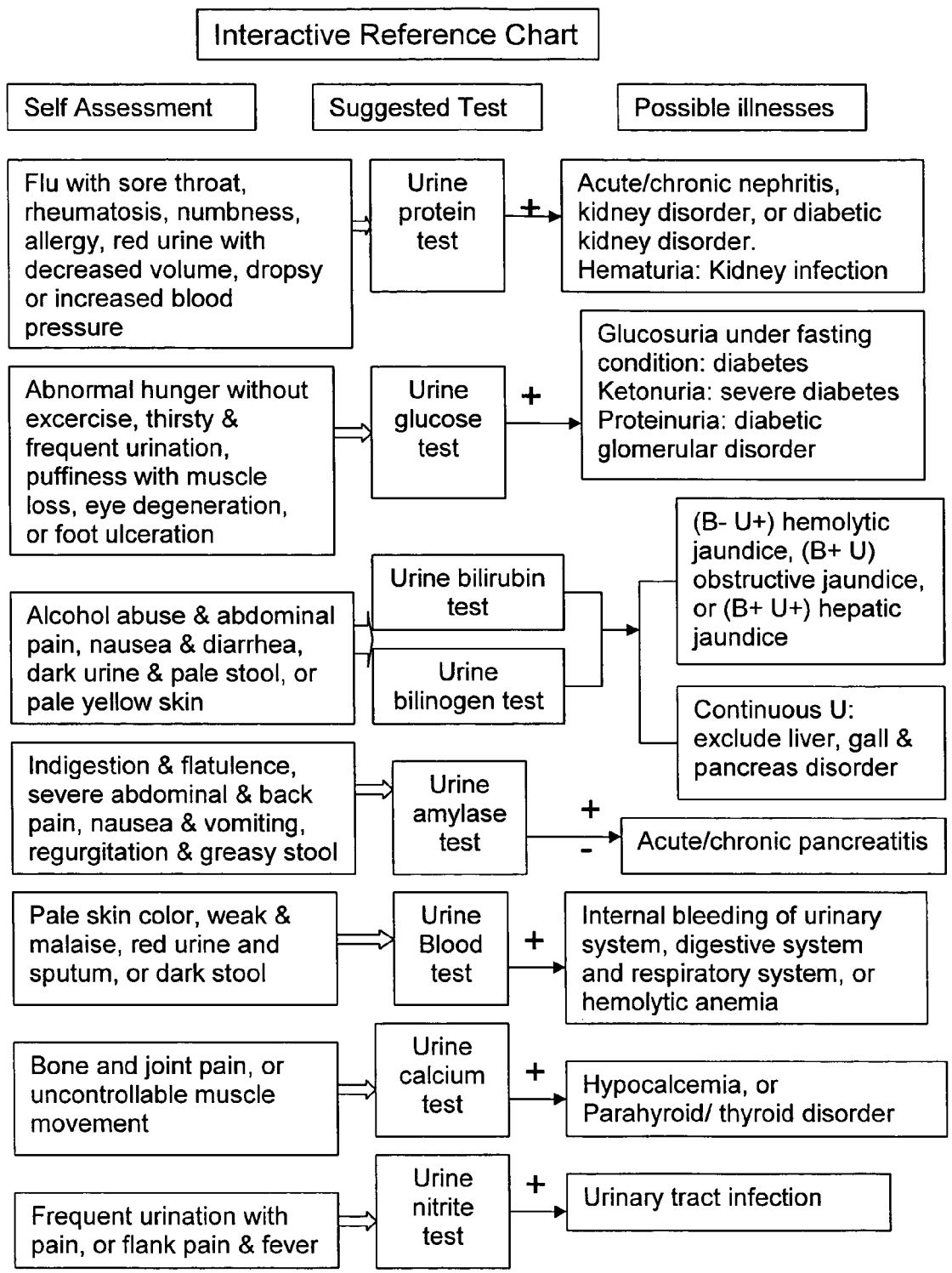
FIG. 5 illustrate an interactive reference chart indicating relationships of possible symptoms of a predetermined number of diseases and the method of use of the preferred embodiment of the present invention.

Referring to FIG. 5 of the drawings, the interactive reference chart indicating possible symptoms of a predetermined number of diseases of the preferred embodiment of the present invention is shown. According to the self assessment of a user, he can choose any units in the medical kit for testing and has a better understanding for his health condition. Seven exemplary illustrations are shown in FIG. 5.

In the first illustrative example, if the user feels like having symptoms of flu with sore throat, rheumatosis, numbness, allergy, red urine with decreased volume, dropsy or increased blood pressure, the urine protein testing composition is suggested to be employed for self testing. A positive test result indicates the possibilities of acute or chronic nephritis, kidney disorder, or diabetic kidney disorder. In addition to hematuria, kidney infection is highly probable.

In the second illustrative example, if the user feels like having symptoms of abnormal hunger without exercise, thirsty and frequent urination, puffiness with muscle loss, eye degeneration, or foot ulceration, the urine sugar testing composition is suggested to be employed for self testing. The presence of glucose in urine under a fasting condition probably represents a high probability of diabetes. If ketone is also found in urine, the condition of diabetes is severe. In addition, if protein is also found in the urine, diabetic glomerular disorder may be developed.

In the third illustrative example, if the user feels like having symptoms of alcohol abuse and abdominal pain, nausea and diarrhea, dark urine and pale stool, or pale yellow skin, the urine bilirubin and urine bilinogen compositions are suggested to be employed for self testing. Generally, a result of Bilirubin negative (B−) representing by a non-blue and non-green color and bilinogen positive (U+) representing by U>1: 20, indicates a possibility of hemolytic jaundice; a result of bilirubin positive (B+) representing by a green or blue color and bilinogen neutral (U) represented by a non-red color indicates a possibility of obstructive jaundice; while a result of bilirubin positive (B+) and bilingoen positive (U+) indicates a possibility of hepatic jaundice. On the other hand, a result of continuous bilinogen neutral (U) of non-red color indicates the exclusion of liver, pancreas, and gall bladder disorder.

In the forth illustrative example, if the user feels like having symptoms of indigestion and flatulence, sever abdominal and back pain, nausea and vomiting, regurgitation and greasy stool, the urine amylase testing composition is suggested to be employed for self testing. A result of non-normal condition represents acute or chronic pancreatitis.

In the fifth illustrative example, if the user feels like having symptoms of pale skin color, weak and malaise, red urine and sputum, or dark stool, urine blood testing composition is suggested to be employed for self testing. A positive testing result is probably representing bleeding of urinary system, digestive system, or respiratory system bleeding, or hemolytic anemia.

In the sixth illustrative example, if the user feels like having symptoms of bone and joint pain, or uncontrollable muscle movement, the urine calcium composition is suggested to be employed for self testing. A decreased calcium level condition, represented by faint or traced opacity, represents hypocalcaemia or parathyroid/thyroid disorder.

In the seventh illustrative example, if the user feels like having symptoms of frequent urination with pain or flank pain and fever, urine nitrite composition is suggested to be employed for self testing. A presence of red color represents a probability of urinary tract infection.

In conclusion, the present invention can be easily carried, conveniently applied in various occasions, and no external factors such as locations, time, climates, and diets variations may affect its application. The user can make self-testing several times daily according to his biologic clock (the regularity of exclusive metabolic substance) thus actively tracing metabolic substances in human body. All enzymes, hormones, metabolic substance of fresh urine with body temperature can be preserved in activity. Therefore, the user can immediately obtain accurate and update information of human body metabolic substances. Colored dots can be marked on different dynamic graphic charts for representing various testing results, by which the user can trace personal physiological function adjustment result such as 'well balance', 'negative', and 'positive' under normal circumstance and make a rational and accurate judgment about his health status. After using the medical test kit of the present invention, the user can perceive roughly his body condition. That is to say, he may know whether he is healthy, sub-healthy, or unhealthy, which kind of illness he is suffering and which stage of chronic illness he is standing, etc. By following the self testing procedure regularly and individually, the user can obtain a vivid impression about his health condition. What is more, he can be aware of pre-warning signals of early stage decay, and pathological decaying factors without any delay, thus gaining the initiative to correct some bad health habits and take more emphasis on health restoration. The update self-testing information provided by patients further facilitated the communication and coordination between the patients and doctors. In addition, the self-testing or tracing can be viewed as contemporary supervision which remarkably reduce the possibilities of misdiagnosis and delayed treatment for some particular chronic illnesses, save a lot of medical expenditure for preventative purposes.

Finally, the present invention transforms traditional testing concepts, and converted hospital hosting preventative medicine to self administering preventative medicine. Its prevalent application and practice undoubtedly make a contribution to social health issue.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure form such principles. Therefore, this invention includes all modifications encompassed within the spirit and scope of the following claims

What is claimed is:

1. A medical test kit, comprising a first plurality of testing compositions including:

a glucose testing composition having 9.8-17.3 w/v % sodium citrate, 5.3-10.0 w/v % anhydrous sodium carbonate, 1.5-1.73 w/v % copper sulfate and a remaining quantity of distilled water;

a protein testing composition having 9.4-10.5 w/v % salicylic sulfate, 38-50 ml distilled water in 100 ml protein testing composition, 0.5-2.0 w/v % sodium chloride, 1.0-3.0 v/v % anhydrous acetic acid and a remaining quantity of 95% methanol;

a blood testing composition having 0.25-1.0 w/v % benzidine, 40-80 ml acetic acid in 100 ml of said blood testing composition, and a remaining quantity of 95% methanol;

a calcium testing composition having 1.5-2.0 w/v % oxalic acid, 1.5-2.0 w/v % oxalic amide, 3.2-3.5 v/v % acetic acid and a remaining quantity of distilled water; and a nitrite testing composition having 0.35-0.45 w/v % sulfanilic acid, 0.2-0.3 w/v % α-naphthyl amide, 1.0-2.0 v/v % methanol, 20-40.0 v/v % acetic acid and a remaining quantity of distilled water; and a first corresponding plurality of interpretation spectra with respect to said glucose testing composition, said protein testing composition, said blood testing composition, said calcium testing composition and said nitrite testing composition respectively, wherein each said testing composition in response to a testing sample reacts to the testing sample for providing a result interpreted by said corresponding interpretation spectrum such that a user is capable of comparing the result and said corresponding spectrum to generate first health condition data.

2. The medical test kit, as recited in claim 1, further comprising a second plurality of testing compositions including:
a bilirubin testing composition having 0.89-1.2 w/v % acid iron chloride, 20.0-25.3 w/v % acetate chloride, 5.0 ml acetic acid in each 100 ml bilirubin testing composition, and a remaining quantity of distilled water;
a bilinogen testing composition having 1.8-2.2 w/v % bimethylbenzaldehyde, 20.0 v/v % concentrated hydrochloric acid, 5.0 v/v % acetic acid and a remaining quantity of distilled water, and
an amylase testing composition having 0.34 w/v % iodine, 0.68 w/v % potassium iodide, 1 v/v % glycerol and a remaining quantity of distilled water; and
a second corresponding plurality of interpretation spectra with respect to said bilirubin testing composition, said bilinogen testing composition, and said amylase testing composition respectively, wherein each said testing composition of said second plurality of testing compositions in response to a testing sample reacts to the testing sample providing a result such that a user is capable of comparing the result and said second corresponding spectrum to generate second health condition data.

3. The medical test kit, as recited in claim 2, further comprising a third plurality of testing compositions including:
a ketone testing composition having 1.24 w/w % sodium nitrofericyanide, 37.04 w/w % anhydrous sodium carbonate, and 61.73 w/w % sulfamine; and
a pH testing composition having 0.01 w/v % phenyl red and a remaining quantity of distilled water; and
a third corresponding plurality of interpretation spectra with respect to said ketone testing composition and said pH testing composition respectively, wherein each of said third composition in response to a testing sample reacts to the testing sample for providing a result such that a user is capable of comparing the result and said third corresponding spectrum to generate third health condition data.

4. The medical test kit, as recited in claim 3, further comprising a dynamic recordation diagram which has an interpretation spectrum, and is arranged to record said first through third health condition data obtained from each of said first, said second and said third plurality of testing compositions, wherein a user is able to compare said first through third health condition data with said dynamic recordation diagram and categorize said first through third health condition data into at least three categories which are healthy condition, doubt condition, and unhealthy condition according to said interpretation spectrum.

5. The medical test kit, as recited in claim 4, further comprising an interactive reference chart having a self assessment portion, a suggested test portion, and a possible illnesses portion wherein said self assessment portion provides information on common symptoms with respect to possible illnesses, wherein said suggested test portion provides a suggestion of said first through third plurality of testing compositions with respect to said common symptoms, such that a user is capable of selecting at least one testing composition from said first through third plurality of testing compositions according to a symptom of said user and guidance from said interactive reference chart.

6. The medical testing kit, as recited in claim 5, wherein said interpretation spectrum of said glucose testing composition has an effective glucose concentration range between 0.03% and 2%, wherein said interpretation spectrum of said protein testing composition has an effective protein concentration range between 0.004% and 0.5%, wherein said interpretation spectrum of said bilirubin testing composition has an effective bilirubin concentration range between 0.125% and 1%, wherein said interpretation spectrum of said bilinogen testing composition has an effective bilinogen concentration range which represents a bilinogen concentration higher than 0.05 and for bilinogen concentration lower than 0.05, wherein said interpretation spectrum of said amylase testing composition has an effective range that at least represents a normal condition, a over active condition, and an inactive condition; wherein said interpretation spectrum of said blood testing composition has an effective blood concentration range between 0.015% and 0.5%, wherein said interpretation spectrum of said calcium testing composition has an effective calcium concentration range between 0.012% and 0.2%, and wherein said interpretation spectrum of said nitrite testing composition has an effective nitrite concentration range between 0.00015% and 0.005%.

7. The medical testing kit, as recited in claim 6, further comprising a plurality of testing tubes corresponding to each of said testing compositions respectively.

8. The medical testing kit, as recited in claim 5, wherein said interpretation spectrum of said glucose testing composition has an effective glucose concentration range between 0.03% and 2% represented by a color range from pale blue, green, yellow, to brown, wherein said interpretation spectrum of said protein testing composition has an effective protein concentration range between 0.004% and 0.5% represented by a color range from little trace white precipitation to heavily white precipitation, wherein said interpretation spectrum of said bilirubin testing composition has an effective bilirubin concentration range between 0.125% and 1% represented by a color range from pale blue green to blue green, wherein said interpretation spectrum of said bilinogen testing composition has an effective bilinogen concentration range which represents a bilinogen concentration higher than 0.05 and for bilinogen concentration lower than 0.05 represented by a color ranged from red to colorless, wherein said interpretation spectrum of said amylase testing composition has an effective amylase concentration range representing a normal condition, an over active condition, and an inactive condition, wherein said interpretation spectrum of said blood testing composition has an effective blood concentration range between 0.015% and 0.5%, wherein said interpretation spectrum of said calcium testing composition has an effective calcium concentration range between 0.012% and 0.2% represented by a color ranged from slight opacity to milky precipitation, and wherein said interpretation spectrum of said nitrite testing composition has an effective nitrite concentration range between 0.00015% and 0.005% represented by a color ranged from cherry-red to dark cherry-red respectively.

9. The medical testing kit, as recited in claim 8, further comprising a plurality of testing tubes corresponding to each of said testing compositions respectively.

10. A method of preparing a medical testing kit, comprising the steps of:
(a) providing a glucose testing composition by reacting 9.8-17.3 w/v % sodium citrate, 5.3-10.0 w/v % anhydrous sodium carbonate, 1.5-1.73 w/v % copper sulfate and a remaining quantity of distilled water to form said glucose testing composition;
(b) providing a protein testing composition by reacting 9.4-10.5 w/v % salicylic sulfate, 38-50 ml distilled water in 100 ml protein testing composition, 0.5-2.0 w/v % sodium chloride, 1.0-3.0 v/v % anhydrous acetic acid and a remaining quantity of 95% methanol to form a protein testing composition;
(c) providing a blood testing composition by reacting 0.25-1.0 w/v % benzidine, 40-80 ml acetic acid in 100 ml of said blood testing composition, and a remaining quantity of 95% methanol to form a blood testing composition;

(d) providing a calcium testing composition by reacting 1.5-2.0 w/v % oxalic acid, 1.5-2.0 w/v % oxalic amide, 3.2-3.5 v/v % acetic acid and a remaining quantity of distilled water to form a calcium testing composition; and (e) providing a nitrite testing composition by reacting 0.35-0.45 w/v % sulfanilic acid, 0.2-0.3 w/v % α-naphthyl amide, 1.0-2.0 v/v % methanol, 20-40.0 v/v % acetic acid and a remaining quantity of distilled water to form a nitrite testing composition; and (f) providing a corresponding number of first interpretation spectra for said glucose testing composition, said protein testing composition, said blood testing composition, said calcium testing composition and said nitrite testing composition respectively such that results obtained from said testing compositions are capable of representing a health condition of a user.

11. The method, as recited in claim 10, further comprising the steps of:

(g) providing a bilirubin testing composition by reacting 0.89-1.2 w/v % acid iron chloride, 20.0-25.3 w/v % acetate chloride, 5.0 ml acetic acid in each 100 ml bilirubin testing composition, and a remaining quantity of distilled water to form said bilirubin testing composition;

(h) providing a bilinogen testing composition by reacting 1.8-2.2 w/v % bimethylbenzaldehyde, 20.0 v/v % concentrated hydrochloric acid, 5.0 v/v % acetic acid and a remaining quantity of distilled water to form a bilinogen testing composition; and (i) providing an amylase testing composition by reacting 0.34 w/v % iodine, 0.68 w/v % potassium iodide, 1 v/v % glycerol and a remaining quantity of distilled water to form said amylase testing composition, and (j) providing a corresponding number of second interpretation spectra with respect to said bilirubin testing composition, said bilinogen testing composition, and said amylase testing solution such that results obtained from said bilirubin testing composition, said bilinogen testing composition, and said amylase testing composition are capable of representing a health condition of said user.

12. The method, as recited in claim 11, further comprising the steps of:

(k) providing a ketone testing composition by reacting 1.24 w/w % sodium nitrofericyanide, 37.04 w/w % anhydrous sodium carbonate, and 61.73 w/w % sulfamine to form said ketone testing composition; and (l) providing a pH testing composition by diluting 0.01 w/v % phenyl red with a remaining quantity of distilled water to form said pH testing composition and, (m) providing a corresponding number of third interpretation spectra with respect to said ketone testing composition and pH testing composition such that results obtained from said ketone testing composition and pH testing composition are capable of representing a health condition of said user.

13. The method, as recited in claim 12, further comprising providing in the kit a dynamic recordation diagram, wherein said dynamic recordation diagram has a plurality of sections with respect to each said testing compositions, and each section has at least three portions representing a healthy condition category, a doubt condition category, and an unhealthy condition category respectively.

14. The method, as recited in claim 13, further comprising providing in the kit an interactive reference chart, wherein the interactive reference chart has a self assessment portion, a suggested test portion, and a possible illnesses portion, wherein said self assessment portion provides common symptoms with respect to possible illnesses and said suggested test portion provides a suggestion of said testing compositions of said medical test kit with respect to the common symptoms such that a user is capable of selecting a correct testing composition.

15. The method, as recited in claim 14, wherein said interpretation spectrum of said glucose testing composition has an effective glucose concentration range between 0.03% and 2%, wherein said interpretation spectrum of said protein testing composition has an effective protein concentration range between 0.004% and 0.5%, wherein said interpretation spectrum of said bilirubin testing composition has an effective bilirubin concentration range between 0.125% and 1%, wherein said interpretation spectrum of said bilinogen testing composition has an effective bilinogen concentration range which represents a bilinogen concentration higher than 0.05 and for bilinogen concentration lower than 0.05, wherein said interpretation spectrum of said amylase testing composition has an effective range that at least represents a normal condition, a over active condition, and an inactive condition; wherein said interpretation spectrum of said blood testing composition has an effective blood concentration range between 0.015% and 0.5%, wherein said interpretation spectrum of said calcium testing composition has an effective calcium concentration range between 0.012% and 0.2%, and wherein said interpretation spectrum of said nitrite testing composition has an effective nitrite concentration range between 0.00015% and 0.005%.

16. The method, as recited in claim 14, wherein said interpretation spectrum of said glucose testing composition has an effective glucose concentration range between 0.03% and 2% represented by a color range from pale blue, green, yellow, to brown, wherein said interpretation spectrum of said protein testing composition has an effective protein concentration range between 0.004% and 0.5% represented by a color range from little trace white precipitation to heavily white precipitation, wherein said interpretation spectrum of said bilirubin testing composition has an effective bilirubin concentration range between 0.125% and 1% represented by a color range from pale blue green to blue green, wherein said interpretation spectrum of said bilinogen testing composition has an effective bilinogen concentration range which represents a bilinogen concentration higher than 0.05 and for bilinogen concentration lower than 0.05 represented by a color ranged from red to colorless, wherein said interpretation spectrum of said amylase testing composition has an effective amylase concentration range representing a normal condition, an over active condition, and an inactive condition, wherein said interpretation spectrum of said blood testing composition has an effective blood concentration range between 0.015% and 0.5%, wherein said interpretation spectrum of said calcium testing composition has an effective calcium concentration range between 0.012% and 0.2% represented by a color ranged from slight opacity to milky precipitation, and wherein said interpretation spectrum of said nitrite testing composition has an effective nitrite concentration range between 0.00015% and 0.005% represented by a color ranged from cherry-red to dark cherry-red respectively.

* * * * *